US011841339B2

(12) United States Patent
Gahlings et al.

(10) Patent No.: US 11,841,339 B2
(45) Date of Patent: Dec. 12, 2023

(54) VOLTAMMETRIC REFERENCE CONTROL SYSTEM

(71) Applicant: ANB Sensors Ltd, Hastingfield (GB)

(72) Inventors: Steven A. Gahlings, Hastingfield (GB); Nathan Lawrence, Hail Weston (GB); Kay Louise McGuinness, Harston (GB)

(73) Assignee: ANB Sensors Ltd, Cambridgesh (GB)

( * ) Notice: Subject to any disclaimer, the term of this patent is extended or adjusted under 35 U.S.C. 154(b) by 502 days.

(21) Appl. No.: 16/755,483

(22) PCT Filed: Oct. 11, 2018

(86) PCT No.: PCT/EP2018/077780
§ 371 (c)(1),
(2) Date: Apr. 10, 2020

(87) PCT Pub. No.: WO2019/072991
PCT Pub. Date: Apr. 18, 2019

(65) Prior Publication Data
US 2020/0264123 A1    Aug. 20, 2020

(30) Foreign Application Priority Data

Oct. 11, 2017  (GB) .................................. 1716652
Oct. 11, 2017  (GB) .................................. 1716660
Feb. 12, 2018  (WO) ................. PCT/IB2018/000097

(51) Int. Cl.
*G01N 27/30*  (2006.01)
*G01N 27/403*  (2006.01)
(Continued)

(52) U.S. Cl.
CPC ......... *G01N 27/301* (2013.01); *G01N 27/302* (2013.01); *G01N 27/308* (2013.01);
(Continued)

(58) Field of Classification Search
CPC .......................... G01N 27/301; G01N 27/4035
See application file for complete search history.

(56) References Cited

U.S. PATENT DOCUMENTS 4,686,011 A     8/1987  Jaeckle
4,822,456 A *   4/1989  Bryan ................ G01N 27/4165
                                                              205/794.5

(Continued)

FOREIGN PATENT DOCUMENTS

DE          19917830 A1    10/2000
WO    WO 2010104962 A1 *   9/2010  ............. G01N 27/30

OTHER PUBLICATIONS

Online Corrosionpedia article entitled "Potentiodynamic" published Sep. 6, 2019. Downloaded Jul. 20, 2022 from https://www.corrosionpedia.com/definition/911/potentiodynamic (Year: 2019).*

(Continued)

*Primary Examiner* — Alexander S Noguerola
(74) *Attorney, Agent, or Firm* — Mughal Gaudry & Franklin PC

(57) ABSTRACT

A voltammetric reference control system for generating a reference signal for an electrochemical sensor. The electrochemical sensor may comprise a voltammetric sensor, a potentiometric sensor, an amperometric sensor, an ion selective sensor and/or the like that is designed to be used in solutions, such as water, seawater, saline solutions and/or the like. The voltammetric reference control system generates a reference potential that does not drift and/or does not require calibration during operation of the electrochemical sensor.

9 Claims, 12 Drawing Sheets

(51) Int. Cl.
*G01N 27/333* (2006.01)
*G01N 27/36* (2006.01)
*G01N 27/416* (2006.01)
*G01N 27/48* (2006.01)
*G01N 33/18* (2006.01)

(52) U.S. Cl.
CPC ........... *G01N 27/333* (2013.01); *G01N 27/36* (2013.01); *G01N 27/4035* (2013.01); *G01N 27/4163* (2013.01); *G01N 27/4165* (2013.01); *G01N 27/4167* (2013.01); *G01N 27/48* (2013.01); *G01N 33/18* (2013.01)

(56) References Cited

U.S. PATENT DOCUMENTS

| | | | |
|---|---|---|---|
| 6,290,829 B1* | 9/2001 | Kato ................... | G01N 27/419 204/426 |
| 8,239,138 B2* | 8/2012 | Hyland .............. | G01N 27/3274 702/65 |
| 2012/0205258 A1 | 8/2012 | Noble | |

OTHER PUBLICATIONS

International Search Report and Written Opinion for International Application No. PCT/EP2018/077780, dated Dec. 21, 2018. (12 pages).

Chun-Yueh Huang, "Design of a Portable Potentiostat with Dual-microprocessors for Electrochemical Biosensors", Universal Journal of Electrical and Electronic Engineering, vol. 3, No. 6, Nov. 1, 2015 (Nov. 1, 2015), p. 159-164.

Chun-Yueh Huang et al., "Integrated potentiostat for electrochemical sensing of urinary 3-hydroxyanthranilic acid with molecularly imprinted poly(ethylene-co-vinyl alcohol)", Biosensors and Bioelectronics, vol. 67, May 1, 2015 (May 1, 2015), p. 208-213.

Christopher Batchelor-Mcauley et al., "Voltammetric Responses of Surface-Bound and Solution-Phase Anthraquinone Moieties in the Presence of Unbuffered Aqueous Media", Journal of Physical Chemistry C, vol. 115, No. 3, Dec. 20, 2010 (Dec. 20, 2010), p. 714-718.

* cited by examiner

VOLTAMMETRIC REFERENCE CONTROL SYSTEM

This application is a U.S. National Stage of International Application No. PCT/EP2018/077780, filed Oct. 11, 2018, which claims the benefit of Great Britain Patent Application No. 1716652.1 filed on Oct. 11, 2017, Great Britain Patent Application No. 1716660.4 filed on Oct. 11, 2017, and International Application No. PCT/IB2018/000097, filed Feb. 12, 2018; the entire disclosures of all are hereby incorporated by reference in their entireties into the present disclosure for all purposes.

BACKGROUND

Embodiments of the present disclosure provide a voltammetric reference control system configured to generate a reference signal potential an electrochemical sensor. The electrochemical sensor may comprise a voltammetric sensor, a potentiometric sensor, an amperometric sensor, an ion selective sensor and/or the like that is configures for operation in low buffering capacity solutions, such as water, seawater, saline solutions and/or the like. The voltammetric reference control system controls reference electrode to generate a reference potential that does not drift and/or does not require calibration during operation of the electrochemical sensor, where the reference electrode comprises a redox chemistry sensitive to proton concentration and the reference electrode is configured to set a pH of the low buffering capacity solution proximal to the reference electrode.

Reference system for an ion selective sensor, for example an electrochemical sensor, a glass electrode, a potentiometric sensor and/or the like. The reference system comprises a reference electrode coupled with a redox active species, wherein the reference electrode is configured in use to contact a low buffer/low ionic strength analyte, such that the redox active species controls the pH of the environment local to the surface of the electrode. In embodiments of the present disclosure, the voltammetric response of the reference electrode, when in contact with a low buffer/low ionic strength analyte, to an applied voltammetric sweep includes a peak or a trough corresponding the pH of the local environment set by the redox active species. Since, the local environment pH set by the redox active species will be constant for the particular redox species and because the voltammetric response, the potential of the peak and/or trough and/or other feature in the voltammetric response, will also be the same for the particular redox species, the reference system will produce an absolute/constant reference measurement that can be used as a reference for any form of ion selective sensor.

In chemistry, pH is a numeric scale used to specify the acidity or basicity (alkalinity) of an aqueous solution. It is approximately the negative of the logarithm to base 10 of the molar concentration, measured in units of moles per liter, of hydrogen ions. More precisely it is the negative of the logarithm to base 10 of the activity of the hydrogen ion. Solutions with a pH less than 7 are acidic and solutions with a pH greater than 7 are basic. Pure water is neutral, being neither an acid nor a base.

pH measurements are important in agronomy, medicine, biology, chemistry, agriculture, forestry, food science, environmental science, oceanography, civil engineering, chemical engineering, nutrition, water treatment and water purification, as well as many other applications.

For nearly a century, pH has most commonly been measured using a glass electrode. The glass electrode is a combination electrode that combines both a glass and a reference electrode into one body. The combination electrode consists of the following parts: a sensing part of the electrode, a bulb made from a specific glass; an internal electrode, usually silver chloride electrode or calomel electrode; an internal solution, usually a pH=7 buffered solution of 0.1 mol/L KCl or $1 \times 10^{-7}$ mol/L HCl; a reference electrode, usually the same type with a reference internal solution, usually 0.1 mol/L KCl; a junction with studied solution, usually made from ceramics or capillary with quartz fiber; and the body of electrode, made from non-conductive glass or plastics.

Glass electrodes cannot be used in many industries because of their fragility, requirement of calibration before use and need to be stored under appropriate conditions. In addition, it is well-known in the art that the reference electrode of the glass electrode, normally a silver/silver chloride system, suffers from drift, such that the measurements from the glass electrode are inaccurate. This issue of drift in reference electrode systems, including the silver/silver chloride reference electrode, is well-known and there is an unmet need in the ion selective/electrochemical sensor industry for a reference system that does not drift.

A number of chemical analysis tools are known from chemical laboratory practice. Such known analysis tools include for example the various types of chromatography, electrochemical and spectral analysis. Particularly, the potentiometric method has been widely used for the measurements of water composition both in the laboratory and in the field of ground water quality control. U.S. Pat. No. 5,223,117 discloses a two-terminal voltammetric microsensor having an internal reference using molecular self-assembling to form a system in which the reference electrode and the indicator electrode are both on the sensor electrode. The reference molecule is described as a redox system that is pH-insensitive (no proton transfer), while the indicator molecule is pH sensitive and is formed by a hydroquinone based redox system having a potential that shifts with the pH. Both, reference molecule and indicator molecule layers are prepared by self-assembly on gold (Au) microelectrodes. In the known micro-sensor, a pH reading is derived from peak readings of the voltammograms.

Recently there has been significant work in the development of pH sensors for use in the water industry, where the concentration of dissolved buffer and/or ionic salt is low. Interest in this area stemmed from the work by Compton et al., (see C. Batchelor-McAuley, B. R. Kozub, D. Menshkau, R. G. Compton, *Voltammetric Responses of Surface-Bound and Solution-Phase Anthraquinone Moieties in the Presence of Unbuffered Aqueous Media*, J. Phys. Chem. C 115, pp. 714-718 (2011)), who showed the use of classical quinone/hydroquinone voltammetry to monitor pH in these systems failed. Compton established that the proton coupled electrochemical process perturbed the pH of the solution locally to the electrode when little or no buffer and/or ionic salt was in the analyte solution. Compton's work suggested the unsuitability of redox active species to measure pH in low buffer analytes.

As well as measuring pH in source water, there is also a need to measure pH in seawater and saline solutions. One important reason for measuring pH in saltwater is to monitor the effects of carbon dioxide in the atmosphere on the pH of the Oceans. As part of its operational definition of the pH scale, the IUPAC defines a series of buffer solutions across a range of pH values (often denoted with NBS or NIST designation). These solutions have a relatively low ionic strength (~0.1) compared to that of seawater (~0.7), and, as a consequence, are not recommended for use in characterizing the pH of seawater, since the ionic strength differences cause changes in electrode potential. To resolve this problem, an alternative series of buffers based on artificial seawater have been developed. This new series resolves the problem of ionic strength differences between samples and the buffers, and the new pH scale is referred to as the 'total scale', often denoted as pHT. The total scale was defined using a medium containing sulfate ions. These ions experience protonation, $H^+ + SO_4^{2-} \leftrightarrows HSO_4^-$, such that the total scale includes the effect of both protons (free hydrogen ions) and hydrogen sulfate ions: $[H^+]T = [H^+]F + [HSO_4^-]$.

Recently there has been significant work in the development of pH sensors for use in the water industry where the concentration of dissolved buffer and/or ionic salt is low. For purposes of clarification, the water industry concerns the monitoring, management, transport and/or of water, which in general does not contain large amounts of ionic salts or dissolved buffer. Traditionally electrochemical pH sensors have focused on either glass electrode or ISFET technologies, which ultimately suffer from the same inherent issue, drift of the reference systems and thereby requiring constant recalibration. Although a solution to the issue on the ISFET has been proposed which uses a second reference electrode species in a controlled environment to account for drift in the primary electrode, the ISFET electrode still needs to be stored under wet conditions and recalibrated after each series of measurement for validation purposes.

Over the past 15 years, work has been performed on developing a pH sensor utilizing traditional hydroquinone/quinone chemistry as the pH sensing element and where reference electrode drift is overcome in the sensor using a species that is insensitive to pH, similar to the microsensor described above. In all of this work, the examples of the species that are insensitive to pH that have been described/used undergo only an electron transfer process, which limit the molecules that can be utilized. Despite this limitation, such insensitive species provide significant advantages over the traditional reference techniques, as the reference systems using the pH insensitive species can be stored dry and do not require a stable external reference electrode; hence the pH sensor using such a reference system can provide for calibrationless operation. The challenge is to find a stable reference compound capable of surviving deployment over a long period of time and/or being insensitive to varying concentrations of species/contamination found within the solution/analyte being tested. To this end a significant amount of focus has been on the use of ferrocene based species, which species undergo a one electron oxidation to the resulting ferricenium ion. Judicious manipulation of the ferrocene structure enhances stability, however polymeric based ferrocene has shown to suffer from electron mobility issues through the ferrocene chain. In addition, several ferrocene molecules have been shown to have redox potentials sensitive to the concentration and type of anion species in the solution/analyte being tested and hence can only be used as a reference when the anion system does not change greatly. In addition, ferrocene reference systems need to be calibrated in the local environment prior to deployment.

A problem for pH sensors, ion selective sensors, glass electrode sensors and electrochemical sensors, is the need for a stable reference electrode. In the glass electrode described herein, the reference electrode in KCl solution can drift during operation making the probe inaccurate. With electrochemical sensors using redox systems, references similar to those used in the glass electrode will also drift. Moreover, use of redox sensitive species that provide an electron, such as ferrocene, as a reference are problematic because the ferrocene is difficult to stabilize on the electrode and the redox potential of the species may drift because of the instability. To-date, the reference electrode has been a major issue with ion selective sensors, electrochemical sensors, glass electrodes and/or the like. Electrochemists often suggest using the power supply as a reference to avoid the issues discussed herein, but even the power source cannot provide a stable reference. In addition, the current reference systems, such as calomel, silver-silver chloride systems and/or the like may not be usable for certain applications as they are bulky, disposed in a chamber behind a frit or the like, and so may not be suitable for sensors for use in confined spaces/locations, such as medical/pharmaceutical sensors, microfluidics and/or the like.

Further embodiments of the present disclosure provide a calibration system for an electrochemical sensor. More particularly, but not by way of limitation, in some embodiments an electrode is provided that is configured to contact a fluid and control the pH of the local environment of the fluid proximal to the electrode, such that a response of the electrode to an applied electrical signal is indicative of the pH of the local environment. In some instances, the fluid contacted by the electrode comprises a reference solution of a reference system of the electrochemical sensor.

Electrochemical sensors are constantly being developed to measure and detect chemicals. Electrochemical sensors essentially fall into three categories: potentiometric sensors, voltammetric sensors and amperometric sensors.

Potentiometric sensors are one of the most common types of electrochemical sensor. Potentiometric sensing is the basis for glass electrodes, which are used for measuring pH, sodium (Na+), potassium (K+), lithium (Li+) and the like, solid membrane electrodes based on the chemical process AgX for X−, liquid membrane electrodes, e.g. electrodes containing a ligand for M+ complexation and used in calcium (Ca+), potassium (K+) sensors and the like, pH-meter-based gas detectors, e.g. carbon dioxide (CO2) sensors and the like, ammonia (NH3) sensors etc., and some solid oxide sensors, e.g. zirconia-based oxygen (O2) sensors and the like. Potentiometric sensors measure a potential difference between an electrode or environment that is sensitive to the desired analyte and an electrode or environment that is insensitive to the analyte. In such sensors, an electrode or environment that is sensitive to the analyte is generally referred to as the sensing electrode and the electrode or environment that is insensitive to the analyte is generally referred to as the reference electrode.

Ion-sensitive field-effect transistors (ISFETs) are a new generation of solid-state potentiometric sensor. In an ISFET, the sensing electrode is replaced with ion selective field effect transmitter, which measures a voltage between a source and a drain that is dependent on a concentration of an analyte in a solution being measured. To process properties of an analyte this source-drain voltage is measured against an output from a reference electrode housed in a well-defined environment.

For both traditional potentiometric and ISFET sensors, significant work has been performed to developing novel sensing electrode to measure different analytes/ions and/or to improve the accuracy/sensitivity for sensing of an ion/analyte. This work has resulted in the development of a range of commercial sensors that can achieve the desired selectivity and sensitivity to measure a range of analytes/ions.

For purposes of this disclosure, potentiometric sensors, ISFET sensors and/or the like are referred to as ion selective electrodes (ISEs) since the sensing electrode in the sensors is tuned to detect/measure a selected ion.

Amperometric sensors measure ion concentration by monitoring the change in current as a function of the analyte. The sensing chemistry or substrate is typically tuned to be selective to the analyte. The sensing electrode is held at a fixed potential with respect to a reference electrode and the analyte (or a product formed from the adducts interaction with the sensor) is oxidized or reduced. This oxidization or reduction changes the current providing for detection of a concentration of the analyte present.

Voltammetric sensors measure ion concentration by measuring a current response as a function of swept potential. Voltammetric sensors are less well-known than, not as commonly used as potentiometric and amperometric based sensors; however voltammetric sensors can provide greater information than single point sensors. In a potentiometric sensor, a potential is swept with respect to a reference electrode and voltammetric peaks arising from oxidation of an analyte (or a product formed from the adducts interaction with the sensor) can be determined from the potential at which the peaks are observed and/or the measured current. The peak data from a voltammetric sensor may be used for detecting/measuring multiple analytes using the same sensor interface, as in metal ion analysis.

Reference electrodes are generally used in all three types of electrochemical sensor to provide a stable, drift-free, accurate value of potential as a reference voltage against which a variable output from the sensor, varying with analyte concentration, is measured. In potentiometric/galvanostatic sensors, such as ISEs and the like, a potential across/between the working and reference electrodes is measured and the current is held at known value. In voltammetric sensors, the potential is swept between the working and reference electrodes and the current output at the working electrode is measured. For amperometric sensors the measured current is determined at the sensing electrode and the potential at the working electrode is held against a reference electrode that is at a stable, set potential.

The standard hydrogen electrode is the reference for standard electrode potentials. The hydrogen electrode contains a platinized platinum electrode immersed in a solution of 1 molar hydrochloric acid (HCl) under a 1 atmosphere (atm) pressure of hydrogen. The hydrogen electrode is extremely accurate, however it cannot be used in operational sensors. Therefore, alternatives have been developed, which are typically based on metals in intimate contact with a sparingly soluble salt of the corresponding cation. The table below highlights some common reference electrode half-cell reactions.

| Electrochemical Reaction | Standard Electrode Potential/V |
|---|---|
| $AgBr + e^- = Ag + Br^-$ | 0.071 |
| $AgCl + e^- = Ag + Cl^-$ | 0.222 |
| $HgO + H_2O + 2e^- = Hg + 2OH^-$ | 0.098 |
| $Hg_2Cl_2 + 2e^- = 2Hg + 2Cl^-$ | 0.268 |
| $Hg_2SO_4 + 2e^- = 2Hg + SO_4^{2-}$ | 0.613 |

The common electrode comprises a silver/silver chloride (Ag/AgCl) or calomel electrode, which is held within a defined environment behind a porous frit that allows for electrical conductivity to the solution that the sensor is measuring. In all cases the activity of all species (metal, sparingly soluble salt) except one (the ion in the solution) should be essentially unity. This is to ensure the reference electrode is stable. However, the porous nature of the salt bridge, which is used to ensure electroneutrality between the reference electrode chamber and the analyte containing solution, means that the properties of the species in the reference chamber can change and the reference potential, as a result, drifts. The salt bridge is porous to provide for electrical conductivity between the two chambers. In practice, a too highly resistive salt bridge should and a too porous salt bridge should be avoided. The latter would allow faster transport of ions and thus alter the conditions of the reference electrode chamber rapidly.

A common system is that of a silver/silver chloride reference system. The Ag/AgCl electrode system is stored in a solution with known properties when not being used to prevent the electrode drying out. The Ag/AgCl sensor requires periodic recalibration due to drifts in the reference electrode potential, as described above. Obviously, as a reference system for an electrochemical sensor, it is essential for accurate measurement by the sensor that the reference system produce a constant reference potential. However, in practice the reference potential may change because the chemistry of the electrode/solution in which the electrode is immersed may breakdown/change and/or because since the frit is porous solutions/analytes can enter the reference system and perturb the reference potential. Furthermore, potentiometric systems typically operate in a continuous single point measurement mode, which is a mode where a known current is held between the reference and sensing electrode (typically 0) and the potential difference is constantly measured and used as an analytical signal. Any changes in the reference system will perturb this measurement mode and cause a drift in the potential difference/reference potential measured and thus affect the accuracy of the measurement.

In use, the reference potential of a conventional reference system drifts when deployed in a solution to be measured due to diffusion of solution through the porous frit into the reference system.

Methods to overcome reference electrode changes/drift have involved, for example, deploying two measurement devices to make separate measurements. The first of these two measurement device methods uses a fast-responding potentiometric system in which the reference electrode is known to drift, and the second method uses an optical measurement to calibrate changes in the reference electrode system. However, the first method requires a system with a fast response time and the second method requires an additional colorimetric system, which adds expense to the sensor.

Testing has shown that a potentiometric system provides a varying output when deployed against a colorimetric system for the measurement of pH in oceans. It has been shown that there is a difference of 0.1 pH units between measured (uncorrected potentiometric) and corrected (against the colorimetric system) potentiometric system output, for a pre-calibrated sensor. This difference in value arises dues to the changes in the reference electrode system of the potentiometric sensor during deployment and shows how erroneous results would have been presented should the colorimetric sensor not been present to recalibrate the sensor in-situ. This method of recalibration although efficient is expensive and would not be suitable for all electrochemical sensor systems, where a suitable colorimetric measurement system may not be available.

Drift in the reference electrode potential during use of an electrochemical sensor is almost impossible to monitor without one of the systems described above, and as a result, the drift in the reference potential may be wrongly assigned to variations in the analyte concentration causing a loss in sensor accuracy. In general, reference electrode drift may be addressed by periodic re-calibration of the electrochemical sensor, which may be performed before every use of the sensor or periodically. However, for long duration/autonomous deployment of an electrochemical sensor without user intervention/calibration, the drift may increase with time making sensor measurements inaccurate and even meaningless. Corrections for reference electrode drift may be made after use of an electrochemical sensor by recalibrating the electrochemical sensor after use, determining changes in the calibration factors before and after of the electrochemical sensor and using the changes in the calibration factors to extrapolate drift-corrected data from the data measured by the electrochemical sensor. In general, linear extrapolation is used to correct the measured data.

Clearly, such extrapolation reduces the accuracy of the electrochemical sensor and for long-duration measurement the accuracy is severely compromised. Additionally, since drift is unlikely to be a linear effect, linear extrapolation can often produce poor drift correction. For regulatory purposes, it is often necessary to calibrate sensors using a standard extrapolation process to ensure for standardized measurements. This can mean that frequent calibration is required and/or that inaccuracy is built into the data. More importantly, the calibration requirement for existing reference systems means that the sensors require constant calibration, which may be expensive and or require user intervention, meaning the sensor cannot be accurately used in an online process and/or autonomously.

Several researchers have taken on the challenge of increasing the stability of the reference electrode and numerous methods have been proposed to overcome the issue.

U.S. Pat. No. 5,419,826 describes an ion-selective reference probe adapted for use with potentiometric measurement systems. The reference probe is non-chloride based and employs a specially adapted electrolyte, which is reversible with regard to ionic activity.

United States Patent Publication Number 20030024812 discloses a solid state electrochemical reference system, containing two or more electrodes, wherein the half-cell potential of at least one electrode is determined by the concentration of a specific ion anticipated to be present in all test solutions. The ion concentration measured in the cell by a first electroanalytical technique does not depend on a known reference electrode potential, such that said electrode, its half-cell potential being calculable from the measured ion concentration, can serve as a reference electrode in one or more subsequent electroanalytical techniques that do depend on a known reference electrode potential, said subsequent technique or techniques being carried out in the same cell.

U.S. Pat. No. 6,398,931 details an improved combination ion-selective electrode apparatus comprising an electrode body, a reference electrode, and an ion-sensing electrode. The reference electrode comprises an ion-permeable junction and a removable membrane cap contains an ion-selective membrane. The membrane cap can be removed from the ion-selective electrode apparatus without endangering the integrity of the reference electrode and is distinct from the ion-permeable junction.

European Patent Number 2 932 249 describes a reference electrode for an electrochemical sensor that comprises an inner reference element, which inner reference element has been embedded into a solid electrochemically active composite material.

U.S. Pat. No. 7,462,267 describes a reference electrode consisting of a metal in contact with an electrolyte containing an anion or cation whose concentration in part determines the redox potential of the electrode. This electrolyte contains a polyelectrolyte that partially and reversibly binds the chemical cation or anion thus lowering the free concentration of the cation or anion compared to the osmotic pressure of the same concentration of cation or anion if present as a simple salt. The polyelectrolyte can be anionic or cationic depending on the chemistry of the redox electrode and a thickener may also be added to the electrolyte.

However, to-date, the proposed techniques for addressing drift of the reference system of electrochemical sensors are complex, require fragile components, require careful handling/operation of the electrochemical sensor, require regular maintenance, require periodic calibration and/or the like, and even using the proposed techniques the detrimental effect of reference system drift may only be masked or may even be compounded.

SUMMARY

In embodiments of the present invention, a redox active species is coupled with a reference electrode and the reference electrode is configured to contact a low buffer and/or ionic strength analyte, such that the redox active species sets the pH of the environment local to the surface of the reference electrode surface. In some embodiments, the reference electrode may comprise a "naked" electrode that is configured for use in a sensor that is configured to be used to measure properties of and/or in a low buffer/low ionic strength analyte. For example, the sensor may be a sensor designed to measure pH of water or seawater or to measure pH or presence of a particular ion in a low buffer/low ionic strength analyte, such as for example a saline solution in a medical system or the like. In other embodiments, the reference electrode may be disposed behind a frit or the like in a chamber containing a low buffer/low ionic strength liquid so that the sensor to which the reference system is attached may be used to measure properties of buffered and/or high ionic strength analytes or the like.

By way of example, anthraquinone, a common redox active species for electrochemical sensors, will set a pH of approximately 10 for the local environment of an electrode when the electrode is disposed in a low buffer and/or low ionic strength analyte and a reducing potential applied to the electrode. In preferred embodiments of the present disclosure, the redox active species is selected to provide a local environment pH for the reference electrode that is not 7, so that the response of the redox active species can be better identified in the voltammetric response of the reference system (low buffer/low ionic strength analytes such as water, seawater, saline solutions and/or the like generally have a pH of 7). In preferred embodiments of the present disclosure, the redox active species may be selected to set a pH local to the reference electrode that is a least one pH unit greater or lower than pH 7. In some embodiments, the redox active species may comprise an acidic or an alkaline chemistry, such as salicylic acid or the like, and as such may set the pH of the environment local to the reference electrode at a distance of greater than one pH unit from pH 7. In some embodiments, a redox active species may be used in conjunction with a chemistry that sets the pH of the low ionic strength/low buffer analyte contacting the reference electrode. For example, a redox active species may be disposed under a layer of an acidic or alkaline chemistry that sets the pH of the environment local to the reference electrode in the low buffer/low ionic strength analyte. In this way, an acidic or alkaline chemistry that sets the pH of the local environment of the reference electrode greater than one pH unit from 7 may be used with a stable redox species that produces a strong voltammetric response.

Previously, in electrochemical sensing, as noted by Compton et al., the fact that a redox species controls the pH of the environment local to an electrode was seen as detrimental, since the redox species in such a system could not be used to measure the actual pH of the analyte. However, it was realized by the inventors of the present system that the effect of the redox active species controlling the pH of the local environment could be used in a reference system, since the pH of the local environment of the electrode when contacted with a low buffer and/or low ionic strength analyte is an absolute determined by the chemistry of the redox active species and the response of the redox active species that pH is also an absolute again set by the chemistry of the redox active species, where the redox active species will produce a voltammetric response to a certain pH that is defined by the chemistry of the redox active species. Sensor configurations have always tried to prevent the reference electrode material controlling/changing the pH of the local environment as this was seen as detrimental to the sensing process. However, applicants have found that reference species that can control the local environment, and in particular the pH of the reference environment, can facilitate the use of pH active and redox active compounds as reference species by using the correct functionalisation and having an understanding of the environment in which the sensor will be immersed.

In some embodiments, the redox active species (sometimes referred to herein as the reference species for conciseness) is configured to control the local environment under certain conditions, where these conditions are provided by the analyte being sensed by the sensor. For example, acidic or alkaline reference species can be used that control the local environment of the reference electrode system when the electrode is being used in water, seawater, saline solutions or the like, where low ionic strength, low natural buffer potential or the like of the analyte provides for the reference species controlling the local environment, where this will not occur with other analytes. In water/seawater/saline solutions or the like, because of the low ionic strength and/or low natural buffer potential, the acidic/alkaline properties of the reference chemistry can be used to set the local pH for the reference electrode to greater than one pH unit from pH7. If, however, the ionic strength and/or natural buffer potential increases in the analyte, water and/or seawater, the pH of the analyte, water and/or seawater will control the environment local to the reference electrode. In such aspects, because the pH properties of the reference species are known, the reference can be used to determine ionic strength and/or natural buffer of the analyte.

In other embodiments of the present disclosure, a calibration system is provided that comprises a calibration electrode, which may comprise a working electrode, that produces a voltammetric electrochemical measurement that is used to verify/calibrate/adjust the reference potential of a reference electrode of an electrochemical sensor.

In embodiments of the present disclosure, the voltammetric electrochemical measurement is used to calibrate/adjust the reference potential to remove/mitigate drift in the reference electrode. In this disclosure, the term "calibrate" is used to describe adjusting a reference potential of a reference system to account for/remove drift and/or changes in properties of the reference system, such as the reference solution and/or the reference electrode.

The calibration electrode is configured in use to contact a solution and to set the pH in the solution local to the surface of the calibration electrode. In some embodiments, the calibration electrode can be disposed in a low buffering capacity solution and/or a reference solution of a reference electrode cell/chamber, as described herein. The calibration electrode comprises an electrode with an active surface that is configured to control the pH of the low buffering capacity solution and/or the reference solution proximal to the working electrode.

The active surface comprises redox functionalities that undergo oxidation/reduction when an electrical signal is applied to the calibration electrode. The redox functionalities produce an electrical response a redox potential, redox current to the electrical signal that depends upon the pH of the reference solution with which the active surface is in contact. More particularly, the response of the redox functionalities depends upon the pH of the local environment of the reference solution proximal to the redox functionalities. Merely by way of example, for some embodiments of the present disclosure, redox functionalities may comprise: quinone, derivatives of quinone, anthraquinone, derivatives of anthraquinone, salicylic acid, derivatives of salicylic acid, nitro groups (nitrobenzene and derivatives), amino groups (amino benzene and derivatives), phenylenediamine based dyes (diphenyl-p-phenylenediamine and derivatives), phenpthiazine based dyes (methylene blue and derivatives), meldola blue, polyanilines, polypyroles, Tetracyanoquinodimethane. In some embodiments, Prussian blue, ferrocene, polyferrocenes, phthalocyanines and/or the like may be used.

In embodiments of the present disclosure, a voltammetric signal or an electrode potential is applied to the calibration electrode. In such embodiments, when the voltammetric signal is applied to the calibration electrode a voltammetric response is generated, where the voltammetric response is produced as result of the pH is the local environment, which is set by the redox species/active surface of the calibration electrode, i.e., is a constant as the set pH produced by the redox species/active surface does not vary. In some embodiments, the voltammetric response may be processed as a voltammogram comprising maxima and/or minima corresponding to a peak oxidation current(s) and peak reduction current(s), respectively. The peaks in the redox current occur at potentials that depend upon the pH set by the active surface.

In embodiments of the present disclosure, the active surface, because of its chemistry/properties, sets a particular pH proximal to the calibration electrode. In some embodiments, the redox functionalities of the active surface may set the local pH. In some embodiments, the redox functionalities in combination with other functionalities of the active surface may set the local pH. In some embodiments, the other functionalities may set the local pH.

As long as the chemistry/properties of the active surface does not change, the pH of the local environment is constant. As such, a response of the calibration electrode to an applied electrical signal, where the response is generated by the redox response of the redox functionalities to the applied signal in the presence of the set pH, is a constant. For example, where the applied signal comprises a voltammetric signal, a voltammogram of the response will include peak potentials corresponding to peak oxidation/reduction currents, with a constant peak potential since the set pH is constant.

In embodiments of the present disclosure, this constant response generated by the calibration electrode to an applied voltammetric signal is used to calibrate a reference electrode of a potentiometric sensor. In some embodiments, a reference potential of the reference electrode is measured and compared to a peak potential from the calibration electrode, and the result of the comparison is used as a baseline measurement. This baseline measurement is used to calibrate the reference electrode when a comparison between the reference potential and the peak potential differs from the baseline measurement, i.e., as the reference electrode's reference voltage drifts.

In some embodiments of the present disclosure, potentials other than the peak potentials are used for calibrating the reference electrode. For example, the voltammogram comprises turning points, locations of greatest change/slope, locations of least change slope, and/or the like that are characteristic of the voltammogram resulting from the set pH and potentials of these locations may also be used or used in addition to the maximum potentials.

In some embodiments, the calibration electrode may be disposed inside the reference cell/chamber of an electrochemical sensor. In such embodiments, when an electrode potential is applied to the calibration electrode, the electrode potential will generate a redox current through the reference solution in the reference cell/chamber. In some embodiments, the electrode potential may be swept between the calibration electrode and the reference electrode in the reference cell/chamber and current between the calibration electrode and a counter/or auxiliary electrode may be measured. In some embodiments, the electrode potential may be swept between the calibration electrode and the reference electrode in the reference cell/chamber, where when the current is suitably low, the reference electrode can as the counter electrode as well. In some instances, a potential of a peak value of the redox current is measured with respect to the reference electrode being used in the potentiometric sensor.

The potential of the peak value depends upon the pH set by the active surface and not on the bulk conditions of the reference solution. Through tracking variations in this measured potential with respect to a potential taken at the onset of deployment, variations in the reference electrode used for the potentiometric measurement will be recorded. Thus, any drifts or changes in reference electrode potential will be known and can be used to recalibrate and modify the data provided from the potentiometric sensor in real-time.

In some embodiments, a processor may control applying electrical signals to the calibration electrode and may use the calibration electrode response to calibrate the reference electrode. In some embodiments, the processor may apply electrical signals to the calibration electrode at the same time or proximal to measurements made by the electrochemical sensor to calibrate each sensor measurement. In some other embodiments, the processor may periodically apply electrical signals to the calibration electrode to periodically calibrate the reference electrode. In such embodiments, calibration may defend on the period the electrochemical sensor is to be used for, the number of measurements to be made, the frequency of measurements and/or the like.

In some embodiments, the electrochemical sensor comprises a reference system comprising a reference electrode disposed in a solution in a liquid chamber, where the reference electrode is disposed behind a porous frit. The reference system may further comprise a bridging system to maintain neutrality in the reference system. In some embodiments of the present disclosure, the calibration electrode is disposed in the solution in the reference system. The solution comprises a reference solution and the active surface of the calibration electrode sets the pH of the reference solution local to the calibration electrode. By applying a voltammetric signal to the calibration electrode a voltammogram is produced with features, such as peak potentials, determined by the local pH. In some embodiments of the present disclosure, a processor or the like compares the potentials of features in a voltammogram produced by the calibration electrode and corrects the reference potential of the reference system for any drift between the reference potential and the potential(s) from the voltammogram.

In some embodiments, other features of the voltammogram produced by the calibration electrode may be used to determine the status/health of the reference electrode. For example, breakdown/changes in chemistry of the solution in the reference system and or the reference electrode may cause changes in the voltammogram produced by the calibration electrode. These changes may include, creation of additional peaks in the voltammogram, changes in overall shape of the voltammogram and/or the like. Detection of these changes can be used to determine when the reference system is no longer functioning properly and can be communicated to a user of the ion selective sensor or generate an alarm/warning.

In some embodiments, calibration of the reference electrode potential is provided by measuring a potential difference between the potential of the reference electrode and a potential of the calibration electrode, which potential is determined by applying a voltammetric sweep between the calibration electrode and the reference electrode, potential of calibration electrode equals attributes of the redox wave which can include the peak maxima onset, half peak height of the voltammetric wave of the eredox active compound. The reference potentialism the potential off the silver\silver chloride couple min contact with the reference solution. where any changes in the potential difference is used to correct/calibrate the output from the sensor. From the potentiometric sweep a characteristic of the sweep—which may be a peak in the voltammetry, a change in direction of the sweep, a maximum rate of change on the sweep or other characteristic that can be ascertained by signal processing—may be used to obtain a potential of the calibration electrode and this potential is used to calibrate the reference electrode. Since the voltammetric electrochemical measurement is not a potentiometric measurement, unlike the measurement from the reference electrode, the measurement provides a truly independent calibration. Moreover, the voltammetric electrochemical measurement may be made periodically reducing issues/maintenance requirements associated with continuous/high frequency measurements. Also, the calibration system may be used with a robust reference system, such as an Ag/AgCl reference system and does not rely on potentiometrically measuring the presence of an ion.

In embodiments of the present disclosure, the calibration electrode comprises a redox species that controls the local environment proximal to the electrode. This control of the local environment may in some embodiments be provided by contacting the electrode with a low buffer/low ionic strength analyte, such as water, seawater or the like. In such, an environment, the calibration electrode, because of the low buffer/ionic strength of the analyte, 'sees' an environment controlled by the redox species itself. For example, a common redox species for electrochemical sensors, anthraquinone will measure a pH of about 10 or 11 when a voltammetric signal is applied because the anthraquinone will consume protons during reduction triggering a change in the local environment that is measured by the sensor. This effect of the redox species will occur for most redox species when the analyte contacted with the redox species is a low buffer/low ionic strength analyte In other embodiments, a redox species containing acid groups, such salicylic acid etc., or alkali groups, such as species containing amine groups, acid groups will create an acidic or alkaline local environment irrespective of the acidity/alkalinity of the fluid being sensed. In such embodiments, the local environment is controlled by the acidic/ alkaline redox species even if the buffer/ionic strength of the analyte contacting the redox species is not low. In some embodiments of the present disclosure, redox species with acid or alkali groups are used to move the pH of the local environment away from a neutral reading, a pH of 7, to provide a known reference potential output from the calibration electrode when a voltammetric signal is applied to the calibration electrode.

Embodiments of the present disclosure may be used for all electrochemical sensors, which require a stable, drift free reference electrode system. For example, potassium ion sensors utilize a valinomycin modified membrane to provide the ion-selective response, in conjunction with a standard Ag/AgCl electrode. The longevity of such systems is often compromised by instability in the reference electrode. In such systems, the addition of a calibration sweep system using an electrode with a controlled environment would obviate the lifetime issues associated with the drift in the reference electrode. Similarly, glass electrodes require constant calibration, in water management operations, this calibration is provided, in general, at least twice a month. Some embodiments of the present disclosure can be configured to replace this manual calibration.

Up until now, the effect of the redox species controlling the local environment has been identified as a weakness in electrochemical sensor operation as it produces incorrect output from the sensor since the sensor measures properties of the local environment, which is controlled by the redox species, not the properties of the solution being tested. However as described herein, the effect provides an electrode that has a known output, due to its control of the local environment, that may be used for calibration.

In sensors designed for use in low buffer/low ionic strength solutions, such as water/seawater or the like, the calibration electrode may be contacted directly with the low buffer/low ionic strength fluid as the redox species/active surface of the calibration electrode can control the pH of the local environment to produce a known/stable potential output from the calibration electrode. In sensors that may be used with fluids with unknown properties and/or high ionic strength/buffer strength, the calibration electrode may be contacted with a known solution, such as a reference solution kept behind a frit or the like, for example an aqueous solution with low ionic/buffer strength. In some other embodiments, the redox species/active surface of the calibration electrode may be tailored to control the local pH of the reference solution. In such embodiments, the calibration electrode may be contacted with the same fluid environment as the reference electrode, i.e., a reference solution held in a reservoir behind a frit that allows for electrical/ion conductivity with the solution being tested/analyzed.

In some embodiments, the calibration system may comprise an additional electrochemical cell/chamber that is placed inside an existing reference electrode chamber. In such an arrangement, the reference electrode in the existing reference electrode chamber may be used as a reference electrode for the calibration system.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 1 shows, in general, a number of related sensor systems comprising a sensor and reference electrode set-up. In detail the systems show in: FIG. 1A) The redox active species may comprise a regular redox active species such as anthraquinone or the like or may be a redox active species that includes directly attached moieties to control the local environment.

FIG. 1B) The reference electrode system comprises a dual layer in which the redox active species is separated/independent from a further chemical species that is used to control the local environment of the reference electrode. FIG. 1C) The redox active/pH active species used within the reference electrode system by virtue of its oxidation or reduction properties can control the pH local to the surface of the reference electrode through the release/loss or gain of protons.

DESCRIPTION

Figure 1:
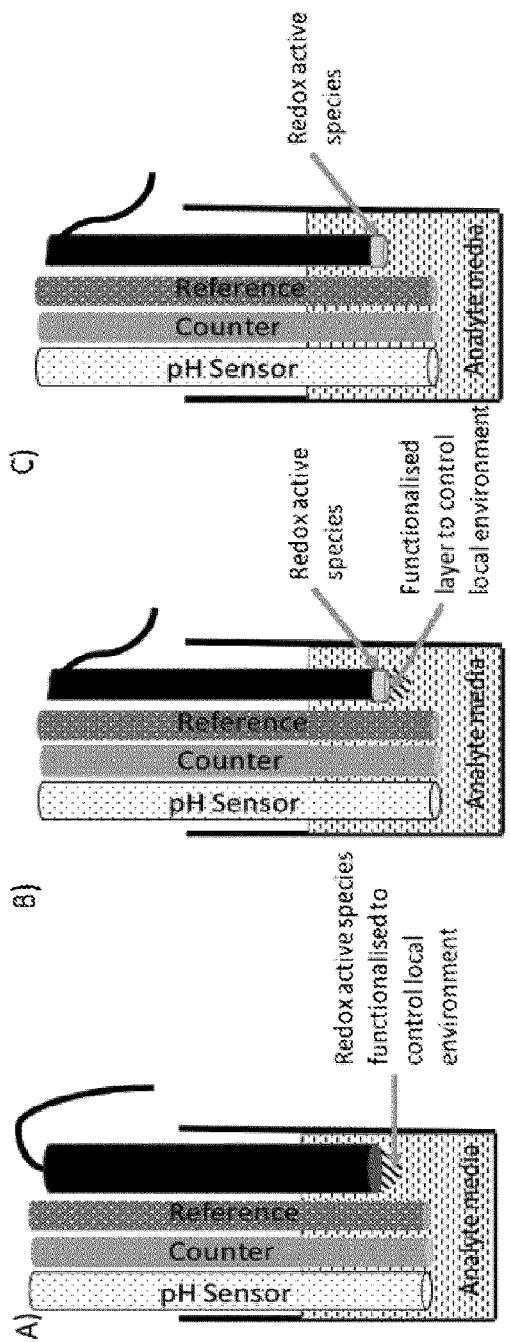

The ensuing description provides some embodiment(s) of the invention, and is not intended to limit the scope, applicability or configuration of the invention or inventions. Various changes may be made in the function and arrangement of elements without departing from the scope of the invention as set forth herein. Some embodiments maybe practiced without all the specific details. For example, circuits may be shown in block diagrams in order not to obscure the embodiments in unnecessary detail. In other instances, well-known circuits, processes, algorithms, structures and techniques may be shown without unnecessary detail in order to avoid obscuring the embodiments.

Some embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure and may start or end at any step or block. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded or transmitted via any suitable means including memory sharing, message passing, token passing, network transmission, etc.

Reference will now be made in detail to embodiments, examples of which are illustrated in the accompanying drawings and figures. In the following detailed description, numerous specific details are set forth in order to provide a thorough understanding of the subject matter herein. However, it will be apparent to one of ordinary skill in the art that the subject matter may be practiced without these specific details. In other instances, well known methods, procedures, components, and systems have not been described in detail so as not to unnecessarily obscure features of the embodiments. In the following description, it should be understood that features of one embodiment may be used in combination with features from another embodiment where the features of the different embodiment are not incompatible.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step. The first object or step, and the second object or step, are both objects or steps, respectively, but they are not to be considered the same object or step.

The terminology used in the description of the disclosure herein is for the purpose of describing particular embodiments only and is not intended to be limiting of the subject matter. As used in this description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting", depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Embodiments of the present disclosure provide a reference electrode system comprising a redox active species that sets the pH of a low buffer/low ionic strength analyte local to the reference electrode surface. A voltammetric response from the redox active species will include features/singularities corresponding to the set pH of the local environment of the reference electrode. These features/singularities in the voltammetric response can be used as a reference for an ion selective/electrochemical sensor. For example, a redox active species will produce a peak redox current at a potential that corresponds to the pH of the local environment of the reference electrode, and this potential can be used as a reference against which measurements from an ion selective/electrochemical sensor can be made.

In embodiments of the present disclosure, the reference electrode is either configured for use in a low buffer/low ionic strength analyte or is disposed behind a frit or the like in a solution of a low buffer/low ionic strength liquid. A voltammetric sweep is applied to the reference electrode and a voltammetric response of the reference electrode is processed. The voltammetric response will include features/singularities with properties that depend upon the pH of the local environment of the reference electrode, and because this pH is set by the redox species the voltammetry response provides a reference from which measurements can be made. In some embodiments, signal processing or the like may be used to measure the properties of the voltammetric response. Advantageously, because the location of the features/singularities can be predicted based upon the pH set by the redox active species and the response of the redox active species to the set pH, weightings can be given to expected locations of features/singularities and used in the signal processing. Additionally, in some embodiments, the voltammetric sweep may be tailored to sweep potentials around expected locations of features/singularities in the voltammetric response.

In embodiments of the present disclosure, the reference system may be used in a sensor configured to measure properties of or detect ions in water, seawater, saline solutions and/or the like having a low buffer/low ionic strength. In other sensors, the reference electrode may be disposed in a reference solution of the low ionic strength/low buffer solution. Advantageously, the voltammetric response of the reference electrode may be used to identify issues with the reference system. For example, appearance of additional features in the sweep may identify contamination/break down of the solution contacting the reference electrode. Large movement of features/singularities in the voltammetric response may also correspond to contamination of the solution contacting the reference electrode or breakdown, loss of the redox active species. In reference systems where the reference electrode is directly in contact with the analyte being tested, changes in the location of features/singularities in the voltammetric response may be used to determine a buffer level/ionic strength of the analyte.

Embodiments of the present disclosure may use the following redox active chemical structures (shown below) for the reference electrode, in which the redox active component molecule comprises carboxylic, sulfonic and/or amino moieties, in conditions in which the buffer concentration within the analyte media does not overwhelm the concentration of acid/base moieties of the redox active component molecule local to the surface; such that the pH of the reference electrode surface is that of the pKa of the moiety.

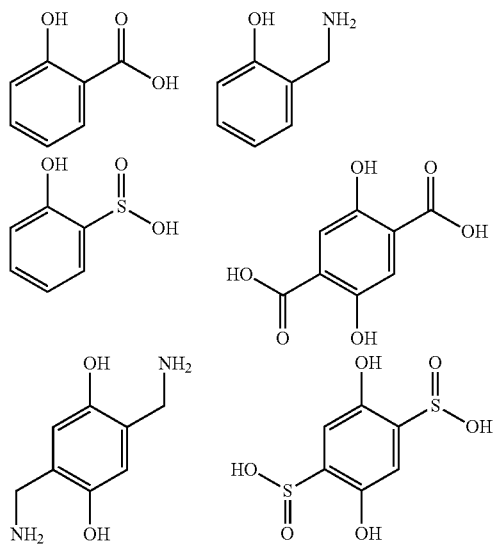

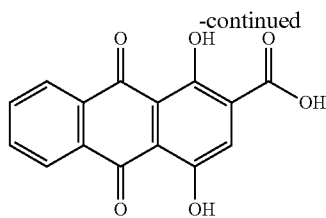
-continued

In certain cases, such as that of salicylic acid (top left structure above), a redox active-pH active polymeric layer can be formed containing carboxylic acid moieties. In certain cases where the buffer concentration of the analyte being tested/sensed does not overwhelm these moieties, the redox active components of the polymer only observes a pH local to the reference system consistent with that of the pKa of the molecule/moieties. Indeed, in certain embodiments of the present disclosure, as described below, a second reference system can be used to provide a qualitative idea of the buffer concentration and a third electrode can be used to determine the pH of the low salinity and/or low buffered media.

While the structures described above illustrate redox active species with "express" acidic or alkaline structures, redox active species such as anthraquinone or derivatives thereof have been found to also set the pH of the local environment of a reference electrode when the electrode was immersed in a low buffer/low ionic strength analyte. This illustrates the versatility of embodiments of the present disclosure, since anthraquinone and derivatives thereof are preferred redox active species because of their stability and consistent/regular and well defined redox response.

FIGS. 1(A)-(C) illustrate an electrochemical pH sensor comprising a reference system in accordance with embodiments of the present disclosure. The reference system is configured for use in a low buffer/low ionic strength analyte media.

In FIGS. 1(A)-(c), the system is run using a conventional electrochemical set-up with external reference and counter electrodes and incorporates the new reference electrode system and a pH sensing electrode. Upon application of a potential ramp, the redox moiety of the reference system will be oxidized and reduced and show a potential consistent with the controlled local environment, whereas the pH sensitive electrode will provide a potential consistent with the pH of the analyte. The difference in the redox potential of the new reference system and the pH sensing electrode provides the pH of the solution, independent of any drift from the external electrochemical reference electrode.

In certain embodiments, the reference electrode system may comprise a single layer in which a redox active species is configured to control the pH of the local environment of the reference electrode. The redox active species may comprise a regular redox active species such as anthraquinone or the like or may be a redox active species that includes directly attached moieties to control the local environment (FIG. 1(A)). In some embodiments, the reference electrode system may comprise a dual layer in which the redox active species is separated/independent from a further chemical species that is used to control the local environment of the reference electrode (FIG. 1(B)). In other embodiments, the redox active/pH active species used within the reference electrode system by virtue of its oxidation or reduction properties can control the pH local to the surface of the reference electrode through the release/loss or gain of protons (FIG. 1(C)), i.e., the redox active species itself acts as the chemistry that sets the pH local environment of the reference electrode.

In FIGS. 1(A) through (C), the reference electrode is described as part of a pH sensor. This has been done merely by way of example as the reference system may be used as part of other types of ion selective/electrochemical sensors. For example, a sensor for electrochemically measuring the presence of an ion in a saline solution, such as for example potassium, nitrogen, sodium and/or the like, may use the reference output from the reference system of the present disclosure as the baseline against which its output is measured. Advantageously, because the reference system of the present disclosure, when used in a sensor being used in a low buffer/low ionic strength analyte media can comprise a naked electrode without a frit of the like, the reference system can be used in microfluidic systems, in-vitro or extra-vitro sensors and/or the like.

The electrode may comprise a conducting/conductive substrate, which substrate may comprise: graphene, carbon nanotubes, carbon, glassy carbon, graphite, diamond, boron doped diamond or the like. The conducting/conductive substrate may comprise a wire, such as a carbon or graphene wire. In some embodiments, a paste/mixture of the redox active species may be formed and coupled with the electrode. For example a paste/mixture of the redox active species formed with carbon may be disposed in a cavity in the electrode. The paste/mixture may include a binder/epoxy to hold the mixture together. In some embodiments the electrode may be produced by printing conductive inks containing the redox active pH sensing material onto a substrate using screen printed, pad printed, flexiographic or rotar gravure printed technologies. Graphene and/or carbon nanotubes have been found as good material for the electrode substrate as they are strong, provide good/regular conductivity, provide for uniform polymerization of the redox active species onto the substrate and can be used in micro-type electrode systems.

Advantageously, the active redox active species may be selected to be insoluble in aqueous media, and therefore may be solvent cast onto the electrode surface. However, in some embodiments of the present disclosure, the active redox active species may be included in a carbon paste or a carbon epoxy, immobilized within an electrode using a carbon press, screen-printed onto an electrode and/or the like. In fact, many of the active redox species described herein may form versatile redox polymers that can be effectively applied to the reference electrode. Merely by way of example, operation of a pH sensor is described for use in ocean and source water environment. Of course, sensors for other analytes in different environments can be used with the reference electrode described herein, but ocean and/or source water environment is one of the most challenging environments for a reference electrode because the water/seawater may contain low natural buffer capacity and/or ionic salt. Indeed, in certain aspects of this invention, described below, a second reference system can be used to provide a qualitative idea of the buffer concentration of the analyte and a third electrode can be used to determine the pH of the low salinity and/or buffered media.

For the environments which have a high buffering capacity and hence would overwhelm the ability of the redox active species to control the pH of the local environment of the reference electrode, the new reference electrode system described herein may be enclosed in a solution having a low ionic strength/low buffer. In some embodiments, the redox active reference electrode may have electrical contact to the analyte media through a porous frit, similar to first used in conventional reference electrode systems.

Figure 2:
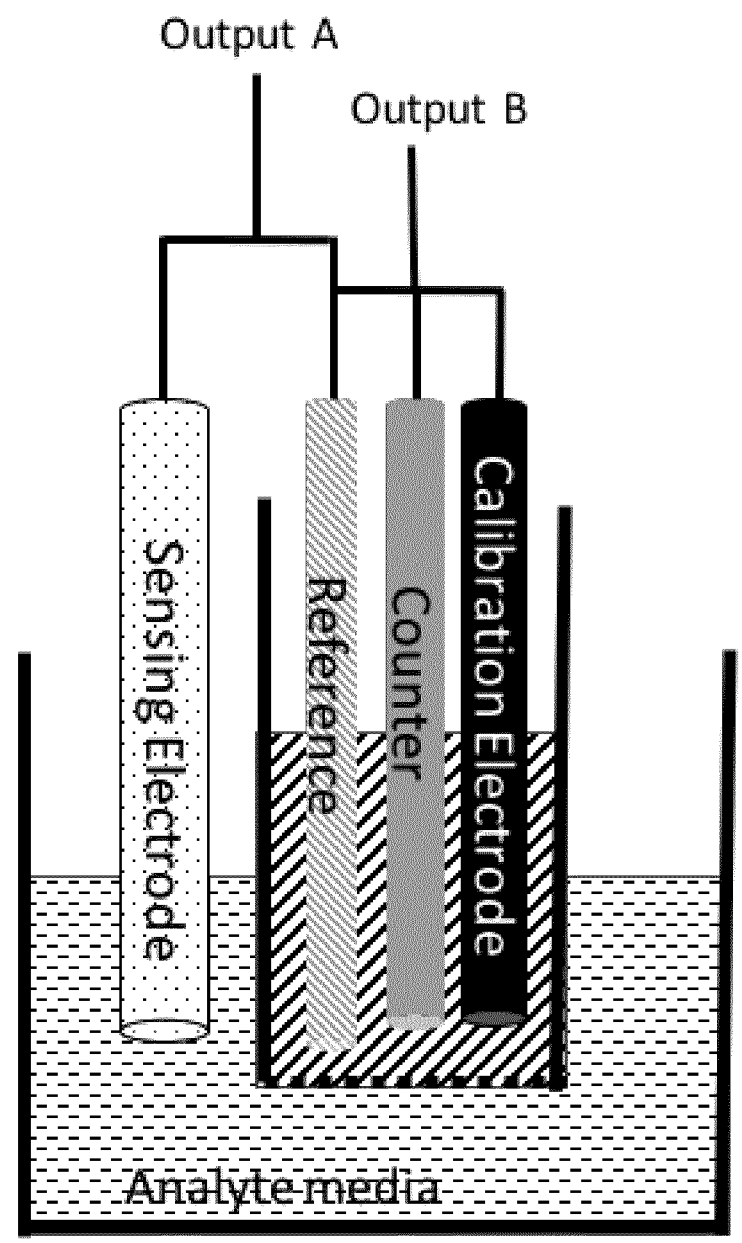
FIG. 2: An electrochemical sensor comprising a reference electrode system in accordance with the present disclosure held with a potassium chloride (KCl) solution and electrically connected to the analyte solution through a frit, wherein the reference electrode system is used as an additional working electrode combined in a three electrode set-up.

FIG. 2 details an embodiment of this architecture in which the new reference electrode system is held within a KCl solution or the like (other low buffer/low ionic strength analytes such as saline solution or the like may be used, but KCL was selected for the example, because it like AgCl is a well-established reference analyte). This design offers a double protection with the local environment resisting perturbations in the bulk changes in the KCL through ion transport across the frit (i.e. it would take dehydration disrupt effective operation of the reference electrode). The system as shown FIG. 2 would be used in the same way as the sensor system described in FIG. 1, in terms of reference system operation. Essentially, the chemistry of the redox active species of the reference electrode sets the pH of the environment in the KCl solution local to the reference electrode and the redox active species records this local pH as a reference which is communicated to the sensor processor The sensor of FIG. 2 may comprise any kind of ion selective or electrochemical sensor. The reference is superior to and meets the long-felt need in the ion selective/electrochemical sensor art, because the redox active species when in contact with the low buffer/low ionic strength analyte media set a pH of the local environment of the electrode, the pH corresponding to the chemical properties of the redox active material, which may contain acidic or alkaline moieties or the oxidation or reduction properties of the redox species (the ability to take up or donate protons).

Figure 3:
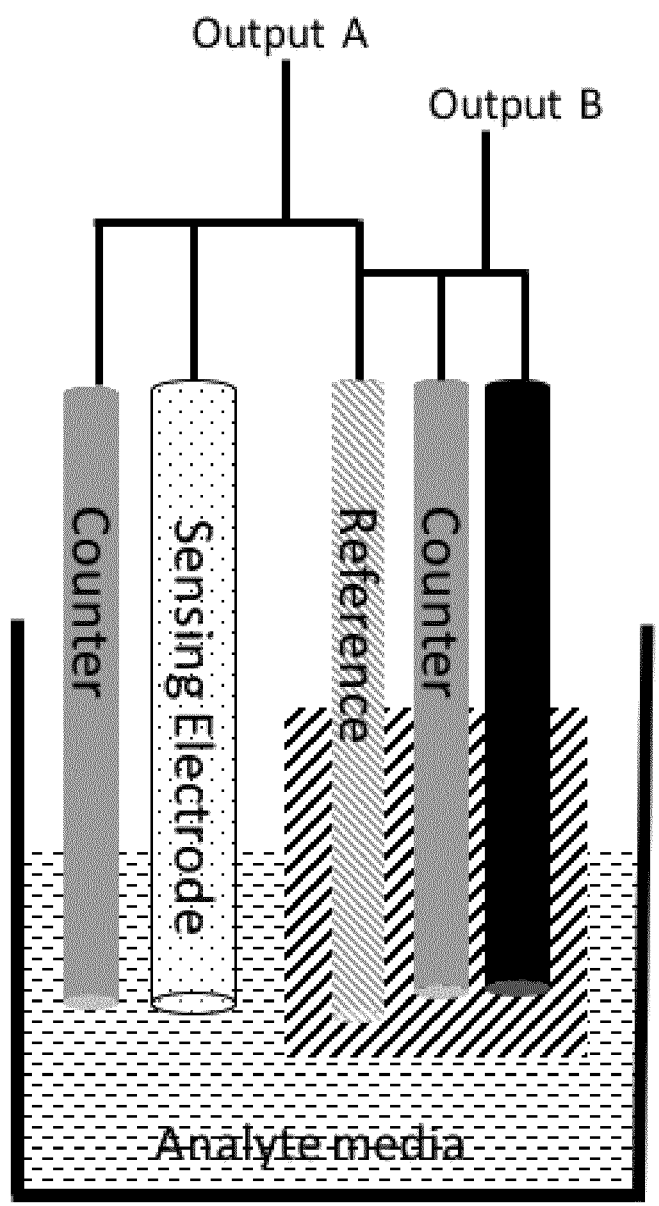
FIG. 3: An electrochemical sensor comprising a reference electrode in accordance with the present disclosure held with a potassium chloride (KCl) solution where the reference electrode is placed behind a frit and used as a classical reference electrode in a three electrode electrochemical system.

In certain cases, the external reference electrode can be replaced with the new reference system, as illustrated in FIG. 3, where the redox active functionalised electrode is placed behind a frit. In this case the redox active species is first oxidized/reduced in a controlled manner to set up a redox potential at the surface of the electrode consistent with the ratio of oxidized to reduced species on the surface. This illustrated system can then be used as a conventional three electrode reference electrode system.

Figure 4:
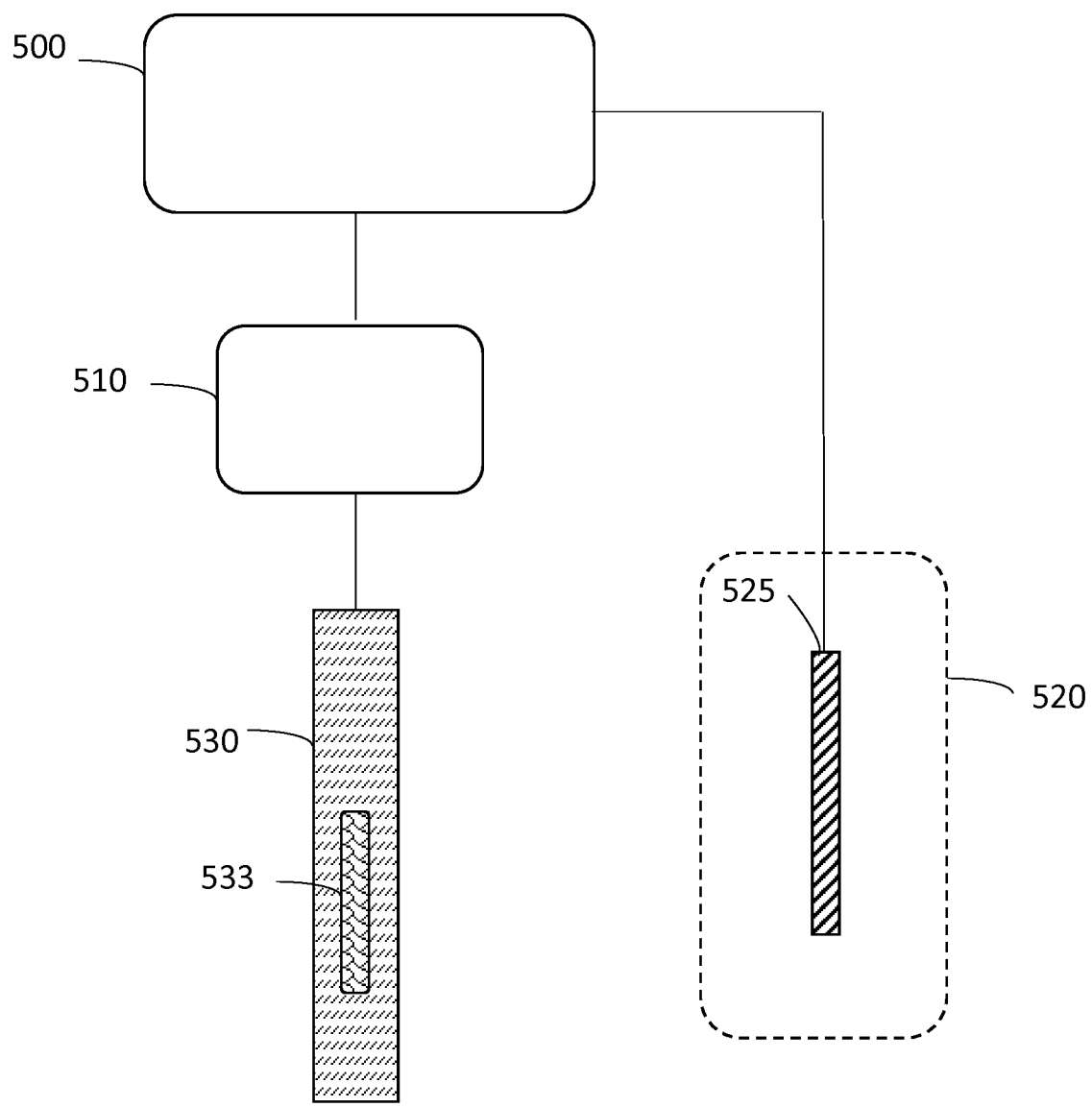
FIG. 4: A flow-type illustration of operation of a reference electrode system in accordance with the present disclosure.

FIG. 4 illustrates a flow-type schematic of use of a reference electrode system in accordance with embodiments of the present disclosure in an electrochemical or ion selective sensor.

In some embodiments of the present invention, a processor 500 may be used to control the operation of a calibration electrode 530 to calibrate a reference electrode 525 of an electrochemical sensor 520.

In a calibration process, the processor 500 may receive a signal from the reference electrode 525 and/or the electrochemical sensor 520 containing a value of a reference potential of the reference electrode 525. The processor 500 may control and/or may be a part of a signal generator/processor 510. Merely by way of example, the signal generator/processor 510 may comprise a potentiostat or the like.

As described herein, the calibration electrode 530 and the reference electrode 525 may be disposed with a reference chamber of the electrochemical sensor 520 and may be in contact with a reference solution therein. In other embodiments, the calibration electrode 530 may be in a separate reference chamber, in a bulk solution being sensed by the electrochemical sensor 520 and/or the like.

As described herein, the calibration electrode 530 comprises a redox active species 533 that is sensitive to a pH of a solution contacting the calibration electrode 530. In some embodiments, the redox active species 533 may comprise an active surface of the calibration electrode 530 that has been modified to provide a redox active functionality. Merely by way of example, in some embodiments, the redox active species may comprise anthraquinone, an anthraquinone derivative, salicylic acid, a derivative of salicylic acid, a combination of anthraquinone and salicylic acid and/or the like.

As described herein, the redox active species 533 is configured to set a pH of a local environment of a solution contacting the calibration electrode 530. This may be provided by contacting the redox active species 533 with a solution having a low buffering capacity, such that it cannot buffer the effect of the redox active species 533 on the local environment. For example, the low buffering capacity solution may comprise water, seawater, a sodium chloride solution, a potassium chloride solution and/or the like. The redox active species 533 may have acidic or basic properties, may comprise acid or base moieties and/or the like.

In some embodiments, the processor 500 may control the calibration electrode 530 to generate a voltammetric signal and to apply this signal to the calibration electrode 530. A response of the calibration electrode 530 to the applied voltammetric signal is communicated to the processor 500 and/or the signal generator/processor 510. The response of the calibration electrode 530 is generated by reduction and/or oxidation of the redox active species 533 in the presence of the solution contacting the calibration electrode 530. Since the pH of the solution is set by the properties of the redox active species 533 and/or any other chemical species on the surface of the calibration electrode 530, the response is characteristic of the set pH of the local environment of the solution proximal to the calibration electrode 530.

In some embodiments of the present disclosure, the processor 500 processes the response to identify features in the response. For example, in some embodiments, the processor 500 may identify a potential of a singularity/peak in the response, where the singularity/peak corresponds to a maximum of the reduction or oxidation current associated with the redox active species 533.

In some embodiments of the present disclosure, the processor 500 may process a difference between the reference potential and the potential associated with the feature in the response and may use this difference to calibrate the reference potential. For example, the reference potential of the electrochemical sensor 520 may be calibrated with the calibration electrode 530 when the electrochemical sensor 520 is set-up/deployed. When the electrochemical sensor 520 is set-up deployed, the reference electrode will, in general, be calibrated to a set reference value. In some embodiments of the present disclosure, when the electrochemical sensor 520 is set-up/deployed, the reference potential of the electrochemical sensor 520 may be communicated to the processor 500 and compared with a peak potential in the response of the calibration electrode 530 to an applied voltammetric signal. This difference, a calibrated difference, may be recorded, entered in a database and the processor 500 may periodically apply further voltammetric signals to the calibration electrode 530 to generate further peak potentials and may compare these peak potentials with reference potentials obtained from the reference electrode 525 and use these comparisons and the recorded/stored calibration difference may be used to calibrate the reference electrode 525.

In the present disclosure control over the local environment can be achieved in two ways: passive control, where the chemical/immobilized layer sets the local environment, or electrochemical control, where the nature of the electrochemical reaction sets the environment local to the surface.

Figure 5:
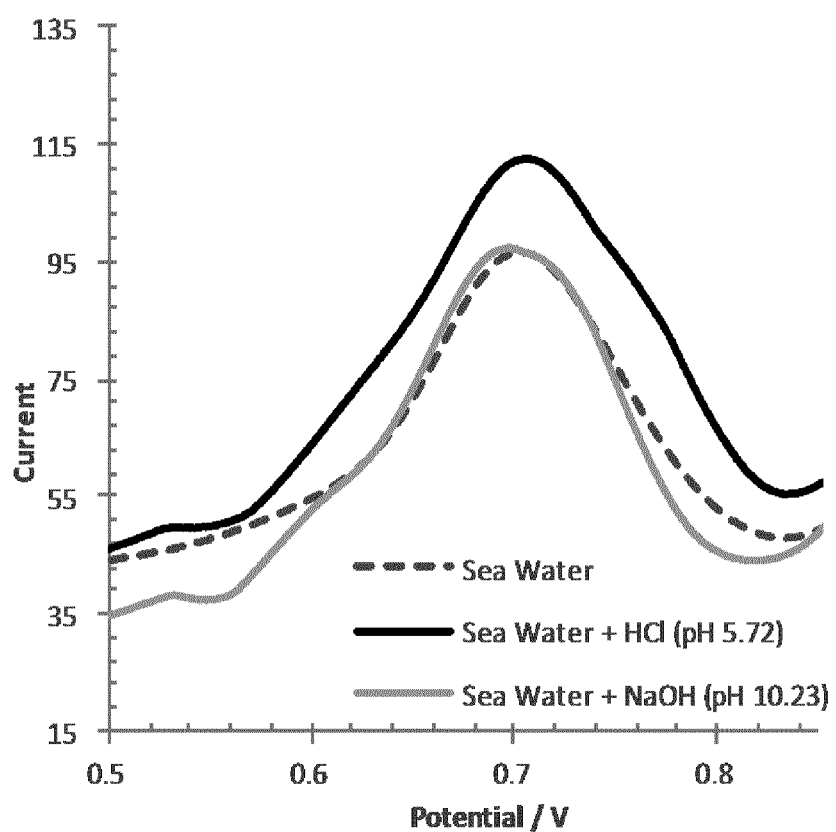
FIG. 5: Response of an electropolymerised salicylic acid electrode when placed in various pH adjusted sea water solutions.
Figure 6:
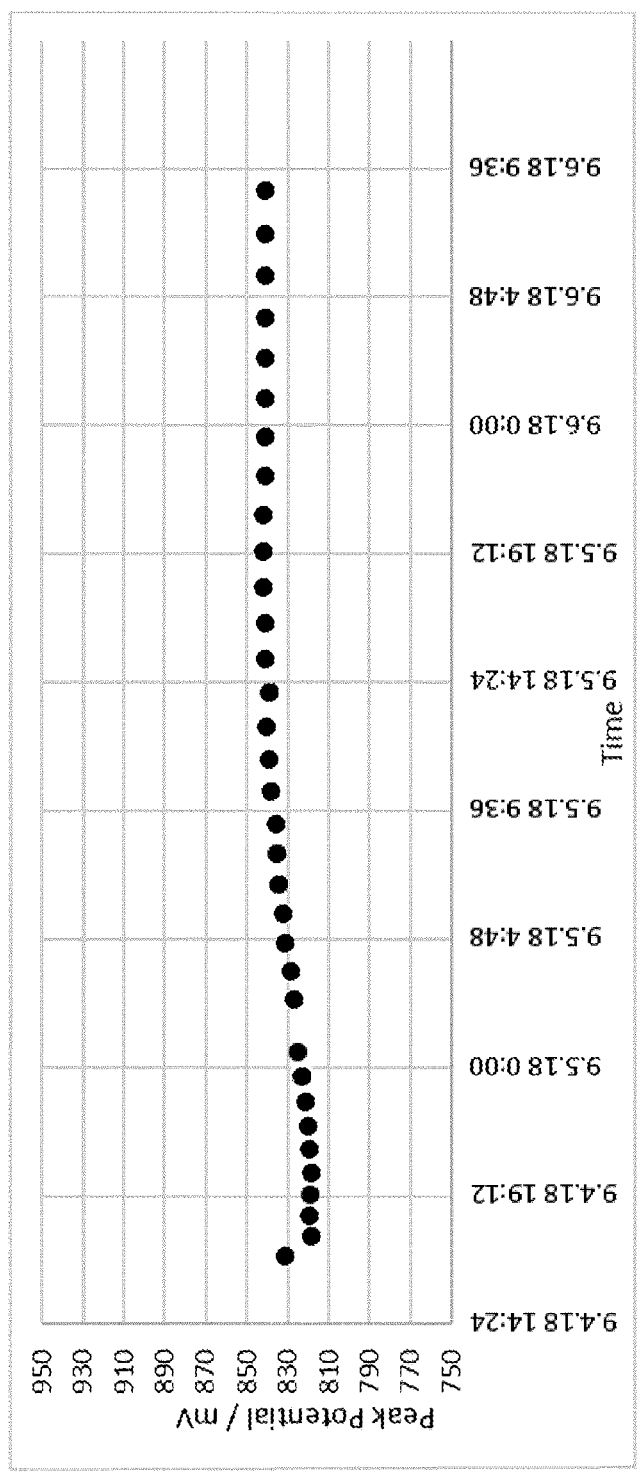
FIG. 6: A plot of peak potential with time, showing little variation in the peak potential upon repetitive scanning.

In the former case, stability of the local environment is achieved without the need for controlling the electrochemical parameters. However, in certain circumstances the electrochemical parameters are tuned to induce electropolymerisation of the surface active molecule to enhance the chemical stability of the electrode. FIG. 5 details the response of a salicylic modified electrode in the presence of sea water and in sea water where the pH has been altered by the addition of acid or base. In this system the salicylic acid is electropolymerised prior to the scans by cycling the potential to potentials where the phenol monomer is oxidized. The redox wave of the resulting polymeric species is found to be stable, consistent with the salicylic acid electrode imparting control over the local environment. The peak potential is set by the pKa of the acid moieties of the molecule. As can further be seen in FIG. 6, which details a plot of peak potential with time, this system shows little variation in the peak potential upon repetitive scanning. The observation of this stable signal shows that the electrochemical parameters do not influence the local environment.

In the second case, where the local environment is controlled by the electrochemical process, control is provided by the electrochemical parameters. In certain embodiments, an electrode is modified with a quinone moiety, which can be electrochemically reduced and subsequently oxidized. During the electrochemical process, protons are consumed local to the environment and as such an alkaline pH is achieved within the diffusion layer of the electrode. Maintaining and/or achieving this alkaline environment is attained by applying a reductive potential to the electrode surface (with respect to the redox potential of the species) or repetitive scanning/cycling of the potential.

Figure 7:
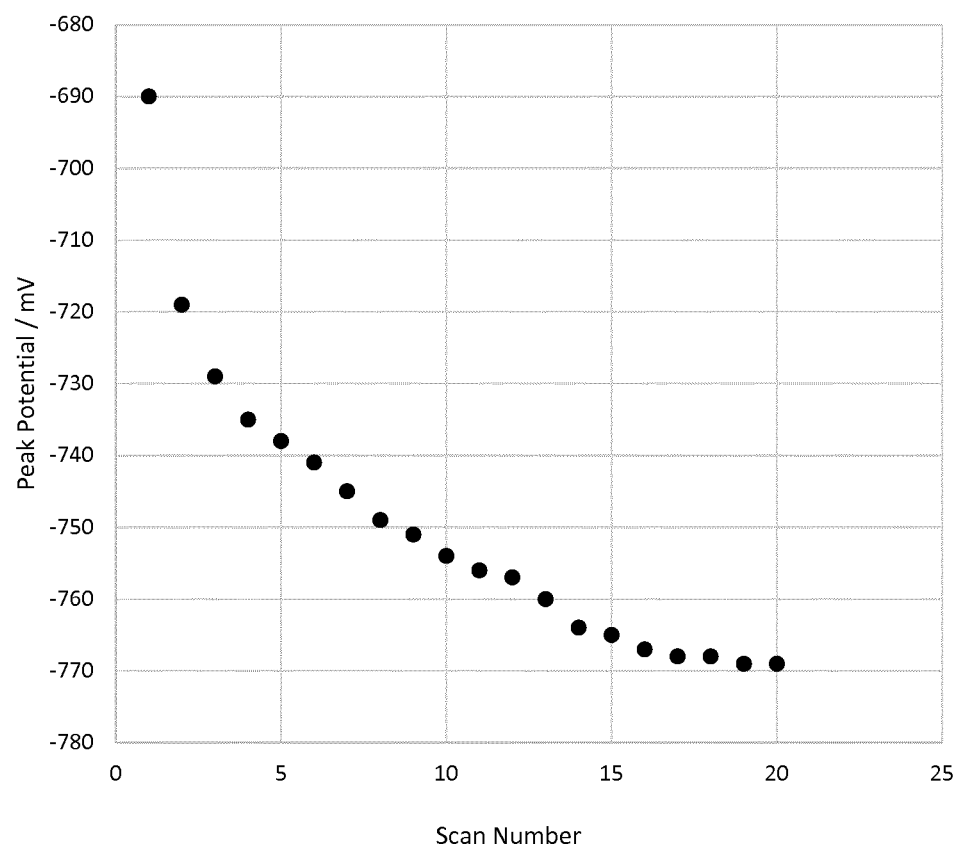
FIG. 7: A plot of peak potential as a function of scan number for a redox active process where the electrochemical process controls the local environment to achieve a reference potential.

FIG. 7 details the plot of peak potential against time showing the peak potential measured for 20 consecutive scans, when the electrode was placed in a pH 10 environment. With each cycle the peak potential is lowered, until it stabilizes between scans 17-20. The data can be explained as follows; the potential is lowered due to the electrochemical process consuming protons at the electrode surface, after each scan the local pH becomes more alkaline as further protons are consumed. The more alkaline the pH, the lower the redox potential of the redox active species for a pH active molecule. Between scans 17 and 20 the local environment is in equilibrium with the electrochemical process and a stable signal is observed. In a real device, control of the system can be achieved through monitoring the peak potential after each scan; as the peak potential converges with repetitive scanning the system will monitor the peak potential until a stable signal is observed across a defined number of scans.

In the case outlined, repetitive scanning was achieved using square wave voltammetry, however other forms of voltammetry: cyclic, linear sweep, normal pulse, differential pulse and elliptical can also be used to sweep the potential. In some systems fixed potential amperometry or fixed current potentiometry may be used to set the local environment prior to the electrochemical sweeps.

The following description provides reference to use of a calibration electrode in accordance with the present disclosure with a glass electrode. This combination is made merely as an example of the operation of the calibration electrode, since glass electrodes are probably the most ubiquitous of electrochemical sensors, and as persons of skill in the art will understand, the calibration electrode may be used in the same manner with any other electrochemical sensor using a reference electrode/system.

Redox active functionalities are functionalities that may be oxidized and reduced, and redox activity may refer to either or both of those processes.

Redox functionalities and/or redox-active functionalities comprise functionalities that are tailored to be sensitive to the presence or concentration of an analyte in a solution. For example, when a voltammetric signal is applied to the tailored redox active functionality, a redox current/potential generated by the redox-active functionalities will depend upon presence or concentration of the analyte in the solution. The solution may comprise of hydrogen ions and in such cases the redox active functionalities are sensitive to the pH of the solution. For most eletrochemical sensors, the redox active functionalities can undergo a reversible electrochemical redox reaction dependent upon the concentration of analyte (hydrogen ions for a pH meter; other analytes for other analyte sensing devices). For a conventional pH sensor, such as the glass electrode, the hydrogen ions associate with the glass membrane causing a change in the measured potential at the electrode housed behind the glass membrane with respect to the reference. In the conventional glass pH electrode, in essence, two Ag/AgCl electrodes are used; one behind the pH sensitive glass and one behind a conventional frit. As such, in some embodiments, therefore the calibration electrode described herein may be used to determine conditions in the chamber behind the glass membrane and/or to calibrate the Ag/AgCl electrode behind the glass membrane.

In a sample solution with an applied electrical potential, for example, where there is a high concentration of hydrogen ions present in a sample solution, the redox reaction occurs at a lower potential. Conversely, where there is a low concentration of hydrogen ions present in a sample solution, the redox reaction occurs at a higher potential. The relationship between these characteristic potentials and the sample solution pH is a function of the chemical identity of the redox active functionality. An algorithm converts electrical potential to pH value to provide a means of determining the pH of an unknown sample.

For some embodiments, redox active functionalities may comprise pH sensitive redox active functionalites such as for example: anthraquinone (AQ), phenanthrenequinone (PAQ), N,N'-diphenyl-p-phenylenediamine (DPPD), anthracene, naphthaquinone, para-benzoquinone, diazo-containing compounds, porphyrins, nicotinamides, including NADH, NAD and N-methylnicotinamide, quinone thiol, monoquaternized N-alkyl-4,4'-bipyridinium, RuO, and Ni(OH).sub.2, and derivatives of those compounds; CO-sensitive ASMs: ferrocenyl ferraazetine disulfide; alkaline metal cation sensitive ASMs: 1,1'-(1,4,10,13-tetraoxa-7,1-diazacyclooctadecane-7,16-diyl dimethyl), ferrocenyl thiol, other ferrocene derivatives containing covalently attached cryptands, and certain metal complexes with Fe.sup.2+/Fe3.sup.+, Co2.sup.+/Co3.sup.+, Cu.sup.+/Cu2.sup.+, ferrocenyl ferraazetine and ferrocenyl cryptands, 1-hydro-1'-(6(pyrrol-1-yl)hexyl-4,4'-bipyridinium bis(hexafluoro-phosphate) and or the like. Further, redox active functionalities that may be activated on a surface of the calibration electrode such as C—O functionalities are described herein.

A reference electrode is an electrode that may be used to establish the potential difference applied to a working electrode of an electrochemical sensor. Generally, reference electrodes comprise a fixed chemical composition and, therefore generate a fixed electrochemical potential. This fixed electrochemical potential provides for measurement of the potential difference applied to the working electrode of the electrochemical sensor. It is imperative that the composition of the reference electrode remains constant, and hence almost no current should be passed through the reference electrode to prevent electrolysis. To prevent passing current through the reference electrode, electrochemical sensors generally comprise a counter electrode to complete the circuit. However, two-electrode electrochemical sensors may be used where the working electrode is a microelectrode. This is possible because the currents passed at the electrode are small.

A working electrode of the electrochemical sensor is the electrode at which the electrochemical process for detecting an analyte of interest occurs. In a sensor, the working electrode may be sensitive to one or more analyte(s) in a test solution, or it may be chemically modified with analyte sensitive species/materials or surface modified so that a surface of the electrode comprises redox active functionalities. The electrochemical response of the working electrode is measured after a perturbation is applied. The perturbation may comprise an electric signal, voltammetric signal and/or the like, for example, application of a potential difference to the working electrode induces electron transfer to occur, and the resulting current at the working electrode can be recorded as a function of the applied potential.

Figure 8:
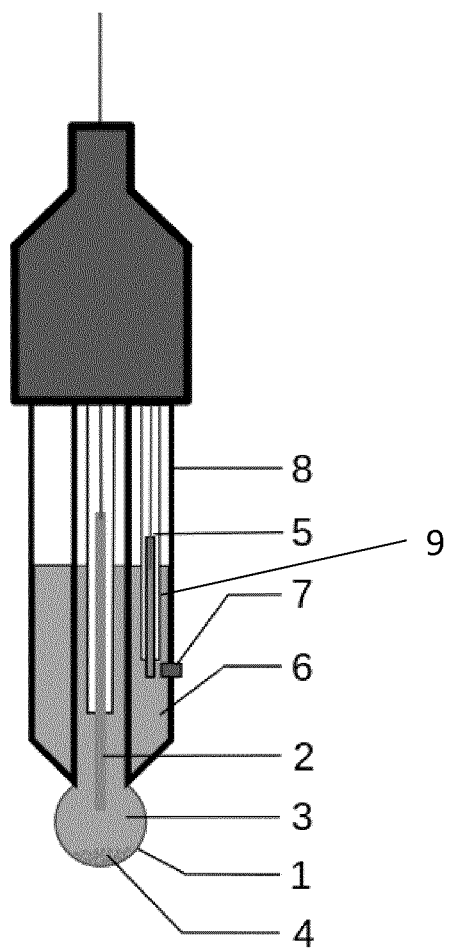
FIG. 8 illustrates a glass electrode pH sensor with a reference electrode.

FIG. 8 illustrates a glass electrode pH sensor with a reference electrode. The glass electrode is essentially a combination electrode, which combines both a glass electrode and a reference electrodes. The glass electrode consists of a sensing part of the glass electrode, often referred to as the sensing electrode which comprises a bulb 1 made from a specific glass, an internal electrode 2 and an internal solution 3. Merely by way of example, the internal electrode may comprise a silver chloride electrode, a calomel electrode or the like. The internal solution 3 may comprise a pH=7 buffered solution of 0.1 mol/L KCl for pH electrodes, 0.1 mol/L XCl for pX electrodes or the like, where X is the ion under determination. In a glass electrode using a silver chloride electrode, a small amount of AgCl precipitate 4 may form inside the glass electrode.

The reference system 5, often simply referred to as the reference electrode, comprises a reference electrode 9 immersed in a reference internal solution 6. The reference electrode may comprise a silver chloride electrode, a calomel electrode or the like. The reference internal solution 6 may comprise a salt such as a silver chloride, potassium chloride or the like. For example, the reference internal solution may comprise 0.1 mol/L KCl or the like.

The glass electrode further comprises a junction 7 that provides for communication between the internal parts of the glass electrode and the solution being analyzed by the glass electrode. The junction 7 may comprise a ceramic, a capillary containing asbestos or quartz fiber and/or the like. The glass electrode comprises a housing 8 housing the components of the glass electrode. The housing 8 may be made from non-conductive glass, plastic and/or the like.

The bottom of the glass electrode balloons out into a round thin glass bulb. The pH electrode is best thought of as a tube within a tube. The inner tube contains an unchanging solution. Also inside the inner tube is the cathode terminus of the reference probe. The anodic terminus wraps itself around the outside of the inner tube and ends with the same sort of reference probe as was on the inside of the inner tube. It is filled with a reference solution and has contact with the solution on the outside of the pH probe by way of a porous plug that serves as a salt bridge.

Figure 9:
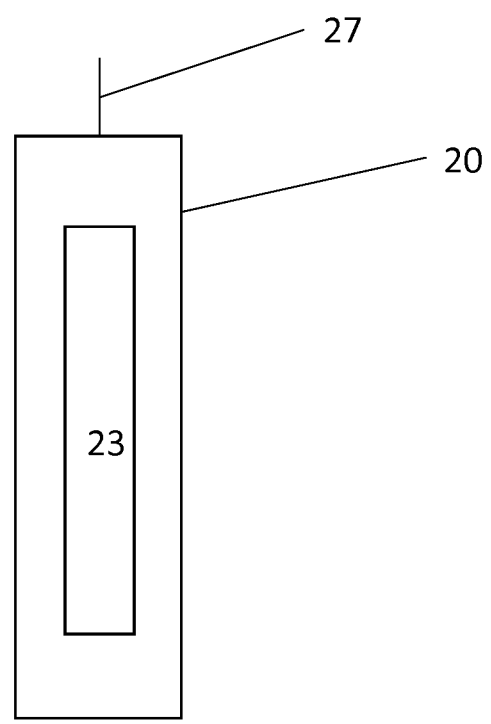
FIG. 9 illustrates an electrochemical sensor system with a calibration system, in accordance with some embodiments of the present disclosure.

FIG. 9 illustrates a calibration electrode in accordance with some embodiments of the present disclosure. The calibration electrode comprises an electrode body 20. The electrode body may comprise carbon, a metal, a metal ion and/or the like. Carbon based electrodes and metallic compounds are commonly used in electrochemistry because of their good electrical conductivity. Carbon materials also have low density, low thermal expansion, and low elasticity and are cost effective, readily available, and suitable for modification. The electrode body in some embodiments may comprise carbon black, graphite, glassy carbon, carbon fibers, carbon nanotubes, multi-walled carbon nanotubes, edge plane carbon, graphene and or the like. Graphene provides a strong electrode with good conductivity and advantageous chemical properties.

The electrode body may comprise a substrate or the like that is connected to an electrical connection 27. The electrical connection 27 may comprise a wire or the like that is configured to communicate electrical signals to and from the calibration electrode.

The calibration electrode comprises an active surface 23. The active surface 23 comprises a surface that is configured to both set the pH of a low capacity buffer solution proximal to the active surface and respond to the set pH proximal to the active surface.

It is known that carbon materials respond to pH without activation. This response is due to the presence of chemisorbed oxygen on the graphite surface that cause the formation of C=O groups. Methods have been developed to modify the carbon materials to improve or tune their electrocatalytic, redox, or ion-sensing properties. These methods of activating the carbon material to provide for the immobilization of pH-sensing substances onto the active surface can be divided into five main groups: (1) chemical modification of the carbon surface with oxygen and/or nitrogen containing functional groups; (2) covalent bonding of pH-sensing compounds onto the active surface initiated either by chemical or electrochemical activation; (3) physical adsorption of pH sensing compounds onto the active surface; (4) fabrication of film electrodes on the active surface; and (5) fabrication of carbon composite electrodes where the surface of the carbon composite comprises pH sensing substances.

Figure 10:
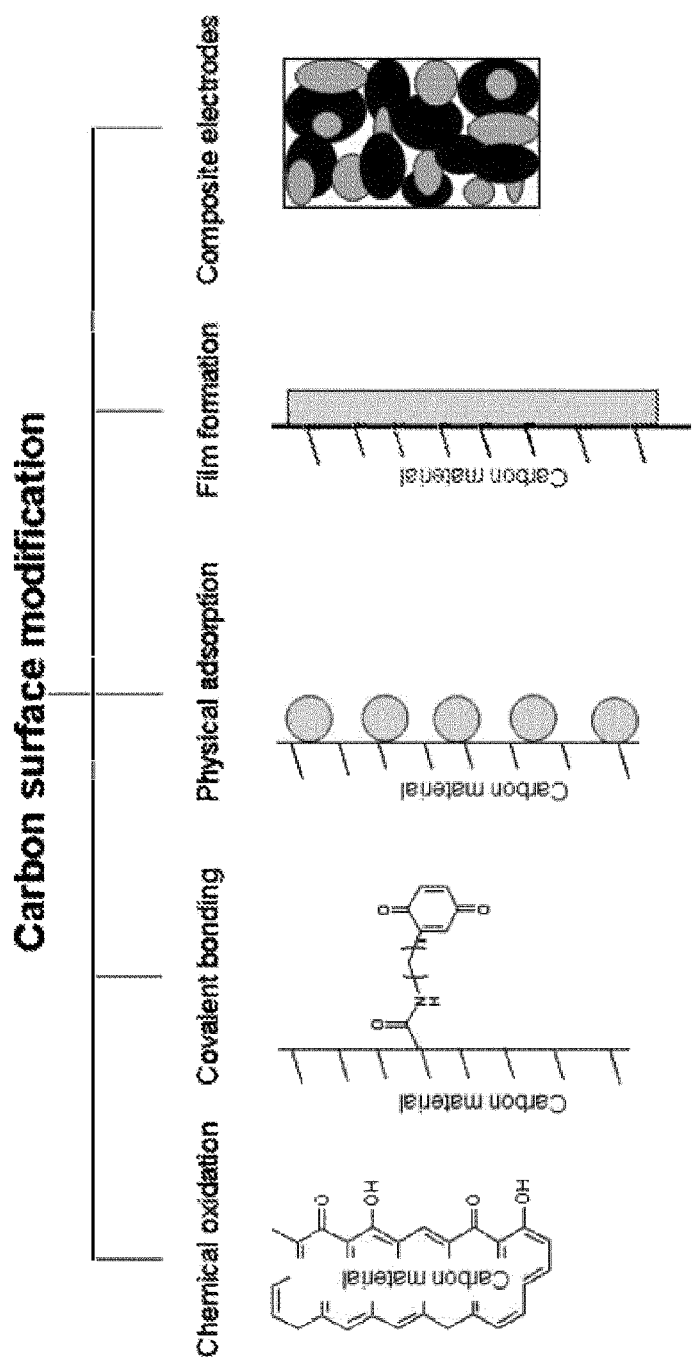
FIG. 10 depicts a schematic representation of a sensor output from an electrochemical sensor comprising a calibration system, in accordance with some embodiments of the present disclosure, using various voltammetric sweep profiles.

FIG. 10 illustrates the active surface 27 formed on the electrode body 23, where the electrode body 23 comprises a carbon material. In some embodiments, the electrode body 23 and the active surface 27 comprise a single substrate and the active surface 23 simply comprises a surface of the electrode body 27 that is configured in use to be in contact with a low buffering capacity solution and/or a reference solution in the reference chamber of the electrochemical sensor. Merely by way of example, the electrode body 27 may comprise a composite electrode and the active surface 23 is simply a surface of the electrode body 27 that is configured to be contacted with the low buffering capacity/reference solution.

In some embodiments, the active surface 23 is configured to be contacted with a low buffering capacity solution. Such solutions, because of low proton transfer rates resulting from their low buffer capacity proximal to the active surface 23, comprise a pH value proximal to the active surface that is set by the properties of the active surface. In some embodiments, the properties of the active surface 23 are configured so that the active surface 23 sets a pH value of a reference solution proximal to the active surface 23. For example, the reference solution may comprise KCl, HCl and/or another salt configured to work with the reference electrode material. In some embodiments, the active surface 23 may have acidic or basic properties so as to set a local pH in the reference solution to a pH above or below a pH of seven (7). In some embodiments, redox active functionalities of the active surface 23 may set the local pH of the low buffering capacity/reference solution.

In embodiments of the present disclosure, the active surface 27 may be metallic Like carbon, a metal may be treated so that substances are formed on a surface of the metal and these substances may comprise substances that will undergo oxidation/reduction in the presence of protons/hydrogen ions such that their electrical response in their presence depends upon a concentration of hydrogen ions, and is therefore indicative of pH. As with the case of a carbon electrode, the electrode body 23 may comprise the metal and the active surface 27 may simply comprise a surface of the electrode body 23 that is configured to be contacted with a low buffering capacity/reference solution.

In some embodiments, the active surface 27 may be formed by a metallic ion disposed in the low buffering capacity solution, where the low buffering capacity solution is a saline solution and then metal ion may produce a redox couple in the saline solution which provides for redox activity at a surface of the electrode body 23.

Boron doped diamond has also been found to be capable of being used to measure pH of a solution. In some embodiments of the present disclosure the active surface 27 may comprise boron doped diamond. When a current is passed through the active surface 27 in the presence of the low buffering capacity/reference solution, a response of the active surface 27 is determined by a hydrogen evolution reaction on the active surface 27, where the reaction is provided by:

$$2H^+ + 2e \rightarrow H_2$$

and, as such is indicative of pH.

The active surface technologies described have been developed to provide an active surface that can be used to measure pH without the need to deposit reagents onto the sensing electrode, i.e., the sensing electrode itself comprises the redox active functionalities. Such technology has been pursued as it removes the issue of coupling reagents with the electrode and to increase the robustness of the sensing electrode. As such, a main drive of the technology has been to increase the redox response of the active surface to increase sensitivity.

As with electrochemical pH sensors using reagents coupled with the sensing electrode, the active surface, like the reagents, will set the pH of a low buffering capacity solution in a region of the low buffering capacity solution proximal to the sensing electrode. Moreover, Applicants have found that the active surface, like the reagents coupled with the sensing electrode, can be configured to set the pH local to the active surface when the active surface is contacted with a reference solution of a reference electrode system. As with electrochemical pH sensors using reagents, this effect has been seen as detrimental to using active surface type electrodes to sense pH of low buffering capacity solutions, such as water, seawater, saline solutions and the like. To avoid this issue, active surfaces have been developed with low concentrations of redox active functionalities so that the pH setting effect of the functionalities is swamped by the pH of the low buffering capacity solution.

In embodiments of the present disclosure, the active surface 27 may comprise a carbon, carbon derivative, boron doped diamond or the like comprising redox active functionalities that are configured to set the pH proximal to the active surface 27 such that when an electronic signal is applied to the active surface 27 a redox response of the active surface 27 is determined by/identifies the pH set by the redox active functionalities.

In embodiments of the present disclosure, the calibration electrode is chemically or physically activated to generate redox active functionalities at the active surface 27. These redox active functionalities are configured to control the local environment of the electrode surface either directly through the introduction of acidic or basic moieties or indirectly through the introduction of redox active moieties, which when oxidized or reduced, take-up or release protons, thus locally changing the pH at the electrode surface.

It has recently shown that mechanical, laser, heat and chemical activation of carbon surfaces (BDD, graphite, carbon nanotube, graphene, glassy carbon, basal plane carbon and edge plane carbon in solid or printed formats) produce electrochemical active sites on the surface of the carbon.

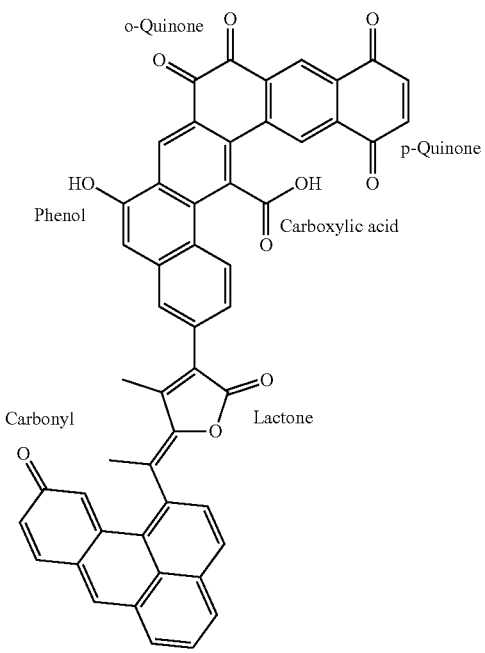 [SMILES: CC1=C(c2ccc3c(c2)cc(O)c2cc4c(=O)c(=O)c5cc6c(=O)ccc(=O)c6cc5c4c(C(=O)O)c23)C(=O)O/C1=C(/C)c1ccc2cccc3cc4c(c1c23)=CC(=O)C=C4]

The carbon chemistry depicted above illustrates the types of functional groups that can be produced on a carbon surface. Research has shown that carbon surface functionalities can provide good pH responses across the entire pH range. In the presence of low buffering capacity media, such as those found within an ion selective electrode reference chamber, which typically contain a known concentration of inert electrolyte (KCl, NaCl, NaClO$_3^-$, Na$_2$SO$_4$ etc.), the pH sensing capabilities of these systems fail and rather than measuring the pH of the low buffering capacity media, a sensor comprising a sensing electrode including carbon surface functionalities will measure the pH set by the carbon surface functionalities. This is because the carbon surface functionalities control the pH local to the electrode surface, due to the intake (or release) of protons by the carbon surface functionalities, making the local environment acidic or alkali.

Figure 11:
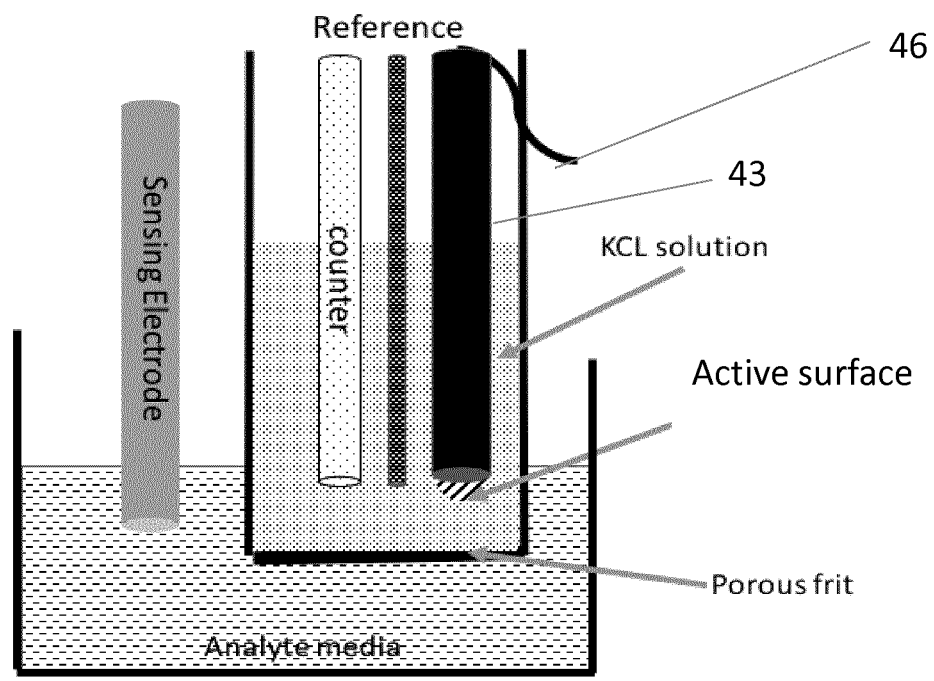
FIG. 11 illustrates an electrochemical sensor comprising a calibration system, according to some embodiments of the present disclosure.

FIG. 11 illustrates an electrochemical sensor comprising a calibration system, according to some embodiments of the present disclosure. In FIG. 11, a novel means of calibrating the electrochemical potential of the reference electrode is provided by the introduction of an additional voltammetric electrochemical measurement.

In FIG. 11, a calibration electrode 43 is placed inside a reference electrode chamber of an electrochemical sensor. A reference electrode for the electrochemical sensor, which is being calibrated, may also be used as a reference electrode for the calibration system, i.e., in the calibration system a voltammetric response of the calibration electrode may be processed against a sweep applied between the calibration electrode, the reference electrode and/or a counter electrode. For example, in some embodiments, the calibration system of the present disclosure may comprise a two or three electrode system. In some embodiments, the reference electrode of the calibration system may comprise the reference electrode of the electrochemical sensor. The two or three electrode system may be used in a voltammetric system to produce a peak potential corresponding to a pH of a solution in contact with the electrodes. Which pH is set by the properties of the calibration electrode.

In some embodiment, prior to deployment of the electrochemical sensor, a voltammetric scan can be taken between the reference electrode and the calibration electrode and a potentiometric measurement recoded by the sensor in a known solution. This initializing scan sets the parameters of the electrochemical sensor taking into account how the particular electrochemical sensor is behaving. In essence, this is a one-time initial calibration for the particular electrochemical sensor. For example, in an ISE, the calibration takes into account how the ion-selective layer responds with respect to the reference electrode, and the voltammetric sweep measures the potential of the reference electrode with respect to the calibration electrode.

In embodiments of the present disclosure, the calibration electrode is chemically or physically activated to generate redox active functionalities on the surface of the electrode. These redox active functionalities are configured to control the pH of the local environment of the electrode surface, either: (a) directly through the introduction of acidic or basic moieties; or (b) indirectly through the introduction of redox active moieties, which when oxidized or reduced, uptake or release proton thus locally changing the pH at the electrode surface. In some embodiments, the redox active functionalities may comprise a combination of those in group (a) and those in group (b).

In some embodiments, the calibration system comprises a counter electrode. However, in some embodiments, when the calibration electrode passes sufficiently low current, the counter electrode may not be required.

In some embodiments of the present disclosure, the calibration electrode may comprise an active surface produced by mechanical, laser, heat and/or chemical activation of a carbon surface, such as boron doped diamond, graphite, carbon nanotube, graphene, glassy carbon, basal plane carbon and edge plane carbon in solid or printed formats.

In embodiments of the present disclosure, the active surface sets the local pH of a low buffering capacity solution and measures this pH to generate a calibration signal that is used to correct drift in the reference potential, this may be or is by means of measuring a voltage and then determining the pH by means of a calibration plot. In embodiments of the present disclosure, the redox active functional groups present on the active surface produce pH local to the active surface that is independent of the ion concentration within the reference electrode chamber.

In embodiments of the present disclosure, a potentiometer 46 or the like may be used to apply a voltammetric signal to the electrochemical sensor and to the calibration system. The electrochemical sensor's response to the voltammetric signal may be used to determine properties, such as concentration, of the selected ion. The calibration electrodes response to the voltammetric signal may be used as a calibration signal to correct for any drift in the reference potential of the electrochemical sensor.

In embodiments of the present disclosure, the calibration system may be used periodically by running a voltammetric sweep against the calibration electrode, which is housed in the reference system behind a porous frit. The response of the calibration electrode to an applied voltammetric signal may take the form of a voltammogram. In some embodiments, a potential of the redox active species, such as a peak potential comprising of a peak in the reduction/oxidation current of the redox active species, is used to correct any drift occurring in the reference electrode. A frequency of voltammetric sweep may be selected in accordance with the application for which the electrochemical sensor is being used. In some embodiments, the electrochemical sensor may be run using a modified bi-potentiostat system.

Figure 12:
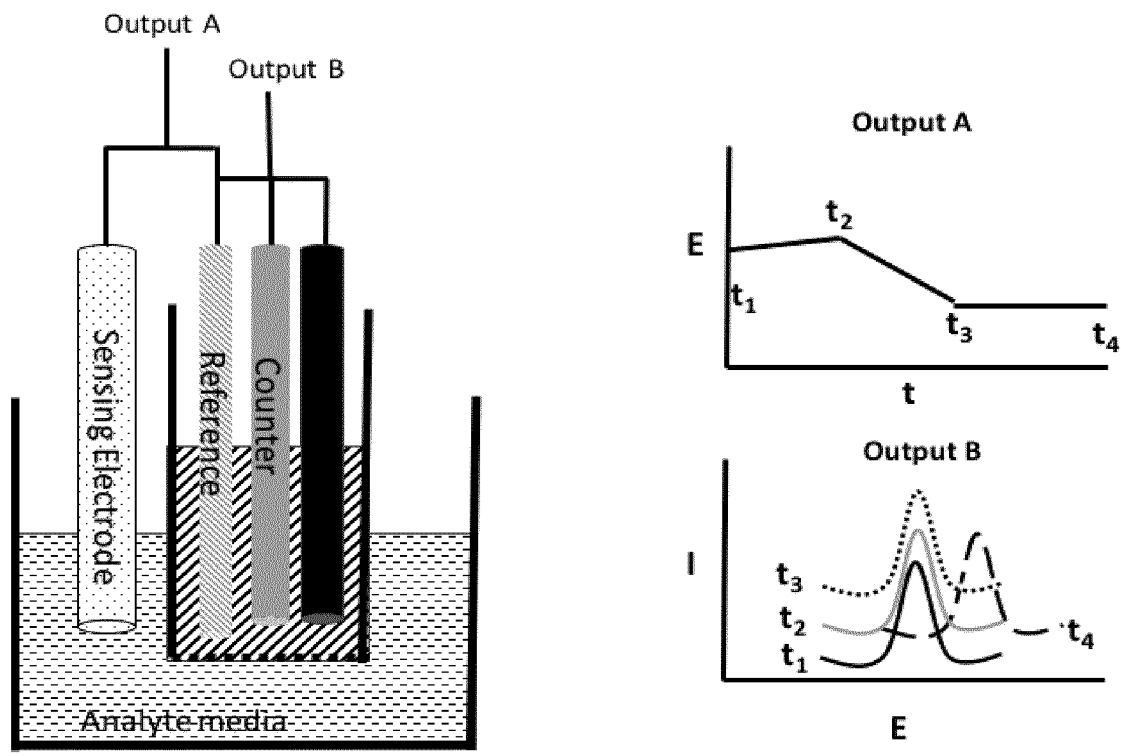
FIG. 12 depicts a schematic representation of a sensor output from an electrochemical sensor comprising a calibration system, in accordance with some embodiments of the present disclosure.

FIG. 12 depicts a schematic representation of a sensor output from an electrochemical sensor comprising a calibration system, in accordance with some embodiments of the present disclosure. In FIG. 12, the electrochemical sensor generates output A at times $t_1$ through $t_1$. The outputs correspond to a selected ion being measured and are determined from a response of the sensing electrode determined using a reference potential of the reference electrode.

Output B illustrates a comparison of the reference potential to a potential obtained from the calibration electrode in response to a voltammetric signal, such as a voltammetric sweep. The potential obtained from the calibration electrode may comprise a potential of a peak oxidation/reduction current produced by the calibration electrode, the redox functionalities on the active surface of the calibration electrode. Since the calibration electrode is maintained in contact with a low buffering capacity solution in the reference system, the calibration electrode sets the pH of the low buffering capacity solution local to the calibration electrode and the potential of the peak reduction/oxidation currents will be constant despite any changes to the low buffering capacity solution.

In general, electrochemical sensor's use reference systems that comprise low buffering capacity solutions such as KCl solution and/or the like so the standard reference solution does not need to be changed for use with the calibration system. While the potential of the oxidation/reduction currents is described for calibration, any reference point in the voltammetric response of the calibration electrode may be used, such as turning points, point of maximum or minimum change in slope of the voltammogram or the like. Further, signal processing methods such wavelet interpretation and or the like may be used to identify reference points in the voltammogram and their corresponding potential for use for calibration of the reference potential. Advantageously, the peak redox/reduction potential of the calibration electrode response may be determined by testing of the electrochemical sensor when built, which may be used for batches of the electrochemical sensor's, or calculated empirically, and this data may be used in the voltammogram analysis. In some embodiments, a potential for either the peak reduction or oxidation current is used to correct the reference potential for drift.

In FIG. 12, a position of the reference potential relative to a peak potential in the voltammetric response of the calibration electrode at time $t_4$ is shown to have shifted with respect to the relative potentials at $t_1$, $t_2$ and $t_3$. Without the calibration system of the present disclosure, this change in the reference potential would have produced an inaccurate measurement at $t_4$. With the calibration system of the present disclosure, however, the drift of the reference electrode can be corrected and the correct measurement of the selected ion processed.

In embodiments of the present disclosure, the calibration system can be used to provide QA/QC of the electrochemical sensor's reference system. As provided in FIG. 11, the electrochemical sensor includes an integrated electrochemical cell/chamber and a potentiostat, and the system uses a voltammetric signal from the potentiostat to produce a sweep between the reference electrode and the calibration electrode in the integrated electrochemical cell/chamber to generate a potential that may be used for QA/QC of the reference electrode during operation of the sensor. The sensor may in some embodiments run using a modified bi-potentiostat system. Such a set-up obviates the need for reference sensor calibration prior to deployment as is the case with current commercial electrochemical sensor's. In embodiments of the present disclosure, prior to deployment, the internal circuit can be measured and this may be used to set the parameters for the reference system.

While the principles of the disclosure have been described above in connection with specific apparatuses and methods, it is to be clearly understood that this description is made only by way of example and not as limitation on the scope of the invention.

The invention claimed is:

1. A method of operating a reference electrode comprising a redox species sensitive to proton concentration, the method comprising:
   contacting a solution with the reference electrode in order to generate a reference potential for an electrochemical sensor;
   using a potentiostat to apply a voltammetric signal to the reference electrode, wherein the reference electrode is one electrode in a three-electrode system in the electrochemical sensor; and
   using a processor to process a voltammogram from a voltammetric response of the three-electrode system to the voltammetric signal and to process the reference potential from the voltammogram, wherein:
      the reference potential corresponds to a maxima or a minima in the voltammogram; and
   a local pH generated in the solution by the redox species is used for at least one of: adjusting parameters of the voltammetric signal applied to the reference electrode or processing the reference potential from the voltammogram.

2. The method according to claim 1, further comprising:
   using the reference potential to process a measurement from the electrochemical sensor.

3. The method according to claim 1, further comprising:
   using the voltammetric response to determine when the reference electrode is either malfunctioning or operating below a threshold performance level.

4. The method according to claim 3, further comprising:
   selecting a different reference electrode and applying the voltammetric signal to the different reference electrode when it is determined that the reference electrode of the three-electrode system is either malfunctioning or operating below the threshold performance level.

5. The method of claim 1, wherein the electrochemical sensor comprises at least one of: a voltammetric pH sensor, an ion selective electrode, an oxidation-reduction potential sensor, and/or a glucose sensor.

6. The method of claim 1, wherein the solution is a low buffering capacity solution.

7. The method of claim 1, wherein the redox species comprises one of salicylic acid, anthraquinone, or an anthraquinone derivate.

8. The method of claim 1, wherein the voltammetric signal comprises a cyclic voltammetric sweep.

9. The method of claim 1, further comprising using the reference potential to calibrate a Ag/AgCl reference electrode of the electrochemical sensor which does not form part of the three-electrode system.

* * * * *